(12) United States Patent
Brown et al.

(10) Patent No.: US 11,633,072 B2
(45) Date of Patent: Apr. 25, 2023

(54) MULTI-PHASE SHAMPOO COMPOSITION WITH AN AESTHETIC DESIGN

(71) Applicant: The Procter & Gamble Company, Cincinnati, OH (US)

(72) Inventors: Mark Anthony Brown, Union, KY (US); Pallavi Mohan Keole, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 128 days.

(21) Appl. No.: 17/174,713

(22) Filed: Feb. 12, 2021

(65) Prior Publication Data

US 2022/0257065 A1   Aug. 18, 2022

(51) Int. Cl.
| | | |
|---|---|---|
| *A61Q 5/02* | (2006.01) | |
| *A47K 5/12* | (2006.01) | |
| *A61K 8/34* | (2006.01) | |
| *A61K 8/41* | (2006.01) | |
| *A61K 8/73* | (2006.01) | |
| *A61K 8/81* | (2006.01) | |

(52) U.S. Cl.
CPC ............ *A47K 5/1211* (2013.01); *A61K 8/342* (2013.01); *A61K 8/416* (2013.01); *A61K 8/737* (2013.01); *A61K 8/817* (2013.01); *A61Q 5/02* (2013.01); *A61K 2800/30* (2013.01); *A61K 2800/413* (2013.01); *A61K 2800/5424* (2013.01); *A61K 2800/5426* (2013.01); *A61K 2800/5428* (2013.01); *A61K 2800/87* (2013.01)

(58) Field of Classification Search
CPC .......... A61Q 5/02; A61K 8/416; A61K 8/342; A61K 8/042; A61K 2800/5428; A61K 2800/87; A61K 2800/5426; A61K 2800/5424; A61K 2800/413; A61K 8/817; A61K 8/737
USPC ........................................................ 424/70.1
See application file for complete search history.

(56) References Cited

U.S. PATENT DOCUMENTS

| | | |
|---|---|---|
| 2,326,733 A | 8/1943 | Fisher |
| 2,396,278 A | 3/1946 | Otto |
| 2,438,091 A | 3/1948 | Lynch |
| 2,486,921 A | 11/1949 | Byerly |
| 2,486,922 A | 11/1949 | Bruce |

(Continued)

FOREIGN PATENT DOCUMENTS

| | | |
|---|---|---|
| AU | 2012337567 B2 | 4/2017 |
| CA | 2143558 A1 | 8/1996 |

(Continued)

OTHER PUBLICATIONS

All Office Actions; U.S. Appl. No. 17/184,814, filed Feb. 25, 2021.

(Continued)

*Primary Examiner* — Eisa B Elhilo
(74) *Attorney, Agent, or Firm* — John G. Powell; Alexandra S. Anoff

(57) ABSTRACT

A container configured to hold a multiphase shampoo composition. The multiphase shampoo composition has a cleansing phase containing a detersive surfactant and a benefit phase containing a gel network. The cleansing phase and benefit phase are visually discrete phases, in physical contact, and form an aesthetic design suspended across at least a portion of the container.

16 Claims, 1 Drawing Sheet

(56) References Cited

U.S. PATENT DOCUMENTS

| | | |
|---|---|---|
| 2,528,378 A | 10/1950 | McCabe, Jr. |
| 2,658,072 A | 11/1953 | Kosmin |
| 2,694,668 A | 11/1954 | Fricke |
| 2,798,053 A | 7/1957 | Brown |
| 2,826,551 A | 3/1958 | Geen |
| 3,152,046 A | 10/1964 | Maria |
| 3,155,591 A | 11/1964 | Harry |
| 3,236,733 A | 2/1966 | Karsten |
| 3,332,880 A | 7/1967 | Adriaan |
| 3,655,096 A | 4/1972 | Easter |
| 3,761,418 A | 9/1973 | Parran |
| 3,852,441 A | 12/1974 | Kooistra |
| 3,929,678 A | 12/1975 | Laughlin et al. |
| 3,940,482 A | 2/1976 | Grand |
| 3,958,581 A | 5/1976 | Abegg |
| 3,959,461 A | 5/1976 | Bailey |
| 3,964,500 A | 6/1976 | Drakoff |
| 4,089,945 A | 5/1978 | Brinkman |
| 4,152,416 A | 5/1979 | Marra |
| 4,197,865 A | 4/1980 | Jacquet |
| 4,217,914 A | 8/1980 | Jacquet |
| 4,323,683 A | 4/1982 | Bolich, Jr |
| 4,345,080 A | 8/1982 | Bolich, Jr. |
| 4,379,753 A | 4/1983 | Bolich, Jr. |
| 4,381,919 A | 5/1983 | Jacquet |
| 4,387,090 A | 6/1983 | Bolich, Jr. |
| 4,422,853 A | 12/1983 | Jacquet |
| 4,470,982 A | 9/1984 | Winkler |
| 4,507,280 A | 3/1985 | Pohl |
| 4,529,586 A | 7/1985 | De |
| 4,565,647 A | 1/1986 | Llenado |
| 4,608,183 A | 8/1986 | Rossmoore |
| 4,663,158 A | 5/1987 | Wolfram |
| 4,666,616 A | 5/1987 | Rossmoore |
| 4,670,430 A | 6/1987 | Imamura |
| 4,686,254 A | 8/1987 | Lochhead |
| 4,704,272 A | 11/1987 | Oh |
| 4,708,863 A | 11/1987 | Bews |
| 4,726,915 A | 2/1988 | Verdicchio |
| 4,788,006 A | 11/1988 | Bolich, Jr. |
| 4,834,767 A | 5/1989 | Helioff |
| 4,885,107 A | 12/1989 | Wetzel |
| 5,034,218 A | 7/1991 | Duvel |
| 5,057,153 A | 10/1991 | Ruggiero |
| 5,104,646 A | 4/1992 | Bolich, Jr. |
| 5,106,609 A | 4/1992 | Bolich, Jr. |
| 5,106,613 A | 4/1992 | Hartnett |
| 5,114,898 A | 5/1992 | Pinnavaia |
| 5,154,847 A | 10/1992 | Lapetina |
| 5,186,928 A | 2/1993 | Birtwistle |
| 5,202,048 A | 4/1993 | Bartolo |
| 5,227,156 A | 7/1993 | Wiese |
| 5,248,445 A | 9/1993 | Rizvi |
| 5,273,189 A | 12/1993 | Jouillat et al. |
| RE34,584 E | 4/1994 | Grote |
| 5,358,667 A | 10/1994 | Bergmann |
| 5,360,581 A | 11/1994 | Rizvi |
| 5,373,973 A | 12/1994 | Foster |
| 5,478,501 A | 12/1995 | Rau |
| 5,518,774 A | 5/1996 | Kappock |
| 5,562,995 A | 10/1996 | Kappock |
| 5,609,862 A | 3/1997 | Chen et al. |
| 5,614,538 A | 3/1997 | Nelson, Jr. |
| 5,674,478 A | 10/1997 | Dodd et al. |
| 5,696,169 A | 12/1997 | Otsu |
| 5,710,114 A | 1/1998 | Pyles |
| 5,726,137 A | 3/1998 | Patel |
| 5,750,122 A | 5/1998 | Evans |
| 5,756,076 A | 5/1998 | Cervantes |
| 5,776,444 A | 7/1998 | Birtwistle et al. |
| 5,785,962 A | 7/1998 | Hinz |
| 5,798,121 A | 8/1998 | Cauwet |
| 5,811,487 A | 9/1998 | Schulz, Jr. et al. |
| 5,836,479 A | 11/1998 | Klima et al. |
| 5,837,661 A | 11/1998 | Evans |
| 5,853,707 A | 12/1998 | Wells |
| 5,854,319 A | 12/1998 | Olenick, Jr. |
| 5,876,705 A | 3/1999 | Uchiyama |
| 5,880,076 A | 3/1999 | Vermeer |
| 5,883,154 A | 3/1999 | Kappock |
| 5,885,948 A | 3/1999 | Glenn, Jr. et al. |
| 5,939,059 A | 8/1999 | Franklin |
| 5,939,203 A | 8/1999 | Kappock |
| 5,955,066 A | 9/1999 | Sako |
| 5,965,515 A | 10/1999 | Rau |
| 5,977,036 A | 11/1999 | Guskey |
| 5,997,851 A | 12/1999 | Cox |
| 6,017,562 A | 1/2000 | Kaufman |
| 6,034,043 A | 3/2000 | Fujiwara |
| 6,162,446 A | 12/2000 | Hani et al. |
| 6,183,766 B1 | 2/2001 | Sine et al. |
| 6,303,109 B1 | 10/2001 | Foerster |
| 6,309,628 B1 | 10/2001 | Ansmann |
| 6,333,040 B1 | 12/2001 | Boyxen |
| RE37,793 E | 7/2002 | Domenico |
| 6,432,420 B2 | 8/2002 | Ellis |
| 6,451,300 B1 | 9/2002 | Dunlop et al. |
| 6,521,238 B1 | 2/2003 | Muller |
| 6,521,239 B1 | 2/2003 | Breton |
| 6,598,762 B2 | 7/2003 | Mckune |
| 6,719,967 B1 | 4/2004 | Brown |
| 6,774,096 B1 | 8/2004 | Paye |
| 6,878,368 B2 | 4/2005 | Ohta et al. |
| 6,908,912 B2 | 6/2005 | Rioux |
| 6,991,799 B2 | 1/2006 | Pham et al. |
| 7,040,311 B2 | 5/2006 | Hochrainer et al. |
| 7,294,611 B2 | 11/2007 | Metrot |
| 7,303,744 B2 | 12/2007 | Wells |
| 7,531,497 B2* | 5/2009 | Midha ............... A61K 8/731 510/147 |
| 7,560,125 B2 | 7/2009 | Ananthapadmanabhan et al. |
| 7,776,347 B2 | 8/2010 | Kerschner et al. |
| 7,855,391 B2 | 12/2010 | Park et al. |
| 8,252,271 B2 | 8/2012 | Singer et al. |
| 8,349,300 B2 | 1/2013 | Wells |
| 8,349,301 B2 | 1/2013 | Wells |
| 8,349,302 B2 | 1/2013 | Johnson |
| 8,361,448 B2 | 1/2013 | Johnson |
| 8,361,449 B2 | 1/2013 | Wells |
| 8,361,450 B2 | 1/2013 | Johnson |
| 8,367,048 B2 | 2/2013 | Wells |
| 8,470,305 B2 | 6/2013 | Johnson |
| 8,653,014 B2 | 2/2014 | Hilvert |
| 8,663,612 B2 | 3/2014 | Gamez-Garcia et al. |
| 8,901,062 B2 | 12/2014 | De Meirleir et al. |
| 8,932,569 B2 | 1/2015 | Garrison et al. |
| 8,940,285 B2 | 1/2015 | Leray et al. |
| 8,969,261 B2 | 3/2015 | Talingting Pabalan et al. |
| 9,005,585 B2 | 4/2015 | Deckner et al. |
| 9,138,429 B2 | 9/2015 | Wise et al. |
| 9,381,382 B2 | 7/2016 | Schwartz et al. |
| 9,393,188 B2 | 7/2016 | Deckner et al. |
| 9,539,444 B2 | 1/2017 | Kinoshita |
| 9,587,209 B2 | 3/2017 | De Meirleir et al. |
| 9,724,283 B2 | 8/2017 | Rizk |
| 9,877,909 B2 | 1/2018 | Cetti et al. |
| 10,143,632 B2 | 12/2018 | Dihora et al. |
| 10,226,782 B2 | 3/2019 | Yamaguchi et al. |
| 10,689,183 B2 | 6/2020 | Moretti |
| 10,912,719 B2 | 2/2021 | Gulbin |
| 10,945,935 B2 | 3/2021 | Brown et al. |
| 2001/0047039 A1 | 11/2001 | Mcmanus |
| 2002/0119113 A1 | 8/2002 | Ellis |
| 2002/0131946 A1 | 9/2002 | Pham et al. |
| 2003/0017126 A1 | 1/2003 | Mahadeshwar |
| 2003/0044471 A1 | 3/2003 | Sakuma |
| 2003/0095938 A1 | 5/2003 | Casero |
| 2003/0119806 A1 | 6/2003 | Lindell |
| 2003/0130145 A1 | 7/2003 | Patel |
| 2003/0138497 A1 | 7/2003 | Sakuma |
| 2003/0171231 A1 | 9/2003 | Shana |
| 2003/0185779 A1 | 10/2003 | Mitsumatsu |
| 2003/0190371 A1 | 10/2003 | Graaf et al. |
| 2003/0215522 A1 | 11/2003 | Johnson |

(56) References Cited

U.S. PATENT DOCUMENTS

| | | |
|---|---|---|
| 2003/0223952 A1 | 12/2003 | Wells et al. |
| 2003/0224954 A1 | 12/2003 | Wells et al. |
| 2003/0224955 A1 | 12/2003 | Ribery |
| 2004/0157754 A1 | 8/2004 | Geary et al. |
| 2004/0191331 A1 | 9/2004 | Schwartz |
| 2004/0197294 A1 | 10/2004 | Seipel |
| 2004/0223941 A1 | 11/2004 | Schwartz |
| 2004/0223991 A1* | 11/2004 | Wei ............ A61Q 19/00 424/401 |
| 2004/0234471 A1 | 11/2004 | Corbella |
| 2004/0266886 A1 | 12/2004 | Seipel |
| 2005/0031569 A1 | 2/2005 | Seipel |
| 2005/0100570 A1* | 5/2005 | Wei ............ A61K 8/11 424/401 |
| 2005/0112083 A1 | 5/2005 | Wells et al. |
| 2005/0143268 A1* | 6/2005 | Midha ............ A61K 8/42 510/130 |
| 2005/0181067 A1 | 8/2005 | Yokoyama |
| 2005/0196368 A1 | 9/2005 | Laurent et al. |
| 2005/0202984 A1 | 9/2005 | Schwartz |
| 2005/0267258 A1 | 12/2005 | Rajaraman et al. |
| 2006/0024256 A1 | 2/2006 | Wells |
| 2006/0024381 A1 | 2/2006 | Schwartz |
| 2006/0045861 A1 | 3/2006 | Bejger |
| 2006/0078524 A1* | 4/2006 | Midha ............ A61K 8/42 424/401 |
| 2006/0078527 A1* | 4/2006 | Midha ............ A61K 8/342 424/401 |
| 2006/0079418 A1 | 4/2006 | Wagner et al. |
| 2006/0079419 A1 | 4/2006 | Wagner et al. |
| 2006/0079420 A1* | 4/2006 | Wagner ............ A61Q 19/10 510/130 |
| 2006/0079421 A1* | 4/2006 | Wagner ............ A61K 8/02 510/130 |
| 2006/0205631 A1 | 9/2006 | Smerznak et al. |
| 2006/0251605 A1 | 11/2006 | Belmar |
| 2006/0269501 A1* | 11/2006 | Johnson ............ A61K 8/342 424/70.28 |
| 2006/0269502 A1 | 11/2006 | Johnson |
| 2007/0095721 A1 | 5/2007 | Davis et al. |
| 2007/0110696 A1 | 5/2007 | Johnson |
| 2007/0110700 A1 | 5/2007 | Wells |
| 2007/0128147 A1 | 6/2007 | Schwartz et al. |
| 2007/0280976 A1 | 12/2007 | Taylor et al. |
| 2008/0039352 A1 | 2/2008 | Wells et al. |
| 2008/0096786 A1 | 4/2008 | Holt et al. |
| 2008/0152611 A1* | 6/2008 | Wells ............ A61K 8/342 424/70.11 |
| 2008/0187507 A1 | 8/2008 | Johnson |
| 2010/0061952 A1 | 3/2010 | Wells et al. |
| 2010/0226868 A1 | 9/2010 | Gamez-Garcia et al. |
| 2010/0234260 A1 | 9/2010 | Sekine et al. |
| 2010/0322878 A1 | 12/2010 | Stella et al. |
| 2010/0330018 A1 | 12/2010 | Lorant et al. |
| 2011/0053818 A1 | 3/2011 | Chuchotiros et al. |
| 2011/0065624 A1 | 3/2011 | Boutique et al. |
| 2011/0067720 A1 | 3/2011 | Ranade et al. |
| 2011/0070180 A1 | 3/2011 | Ranade et al. |
| 2011/0081392 A1 | 4/2011 | de Arruda et al. |
| 2011/0110991 A1 | 5/2011 | Garrison et al. |
| 2011/0248052 A1 | 10/2011 | Kelly et al. |
| 2012/0148644 A1 | 6/2012 | Popplewell et al. |
| 2012/0164198 A1 | 6/2012 | Johnson et al. |
| 2012/0308502 A1 | 12/2012 | Wise et al. |
| 2012/0329768 A1 | 12/2012 | Wise et al. |
| 2013/0029894 A1 | 1/2013 | Bettiol et al. |
| 2013/0090279 A1* | 4/2013 | Hilvert ............ A61K 8/41 510/125 |
| 2013/0131188 A1 | 5/2013 | Beckedahl et al. |
| 2013/0143784 A1 | 6/2013 | Rizk |
| 2013/0171216 A1 | 7/2013 | Alden-danforth et al. |
| 2013/0174863 A1 | 7/2013 | Marsh et al. |
| 2013/0243717 A1 | 9/2013 | Catalan et al. |
| 2013/0243835 A1 | 9/2013 | Tanner et al. |
| 2014/0018276 A1 | 1/2014 | Coffindaffer et al. |
| 2014/0099276 A1 | 4/2014 | Yang et al. |
| 2014/0112964 A1 | 4/2014 | Wu |
| 2014/0162931 A1 | 6/2014 | De Meirleir et al. |
| 2014/0335041 A1 | 11/2014 | Peffly et al. |
| 2015/0010487 A1 | 1/2015 | Snyder et al. |
| 2015/0011450 A1 | 1/2015 | Carter et al. |
| 2015/0044157 A1 | 2/2015 | Kulkarni et al. |
| 2015/0059795 A1 | 3/2015 | Vatter et al. |
| 2015/0093422 A1 | 4/2015 | Garrison et al. |
| 2015/0102061 A1 | 4/2015 | Larson et al. |
| 2015/0313833 A1 | 11/2015 | Hilvert et al. |
| 2015/0342842 A1 | 12/2015 | Wise et al. |
| 2015/0374609 A1 | 12/2015 | Cetti et al. |
| 2016/0067172 A1 | 3/2016 | Burch et al. |
| 2016/0106663 A1* | 4/2016 | Gulbin ............ A61K 8/922 424/401 |
| 2016/0143827 A1 | 5/2016 | Castan Barberan et al. |
| 2016/0256365 A1 | 9/2016 | Dihora et al. |
| 2017/0216158 A1 | 8/2017 | Deckner et al. |
| 2017/0225183 A1 | 8/2017 | Kelly |
| 2017/0333734 A1 | 11/2017 | Mauer et al. |
| 2017/0367955 A1 | 12/2017 | Brown et al. |
| 2018/0071185 A1 | 3/2018 | Cochran et al. |
| 2018/0098923 A1 | 4/2018 | Hutton, III |
| 2018/0339845 A1 | 11/2018 | Moretti |
| 2019/0105246 A1* | 4/2019 | Cochran ............ A61K 8/89 |
| 2019/0105247 A1* | 4/2019 | Song ............ A61K 8/466 |
| 2019/0201925 A1 | 7/2019 | Toh et al. |
| 2019/0290554 A1 | 9/2019 | Yokogi et al. |
| 2019/0290555 A1 | 9/2019 | Yokogi et al. |
| 2019/0290562 A1 | 9/2019 | Yokogi et al. |
| 2019/0290567 A1 | 9/2019 | Yokogi et al. |
| 2019/0290568 A1 | 9/2019 | Yokogi et al. |
| 2019/0307665 A1 | 10/2019 | Yokogi et al. |
| 2019/0365611 A1 | 12/2019 | Brown et al. |
| 2020/0188243 A1* | 6/2020 | Brown ............ A61K 8/0254 |
| 2021/0022975 A1 | 1/2021 | Cochran et al. |
| 2021/0045979 A1 | 2/2021 | Dunlop et al. |
| 2021/0121903 A1 | 4/2021 | Yamaguchi et al. |
| 2021/0253303 A1 | 8/2021 | Bartolucci et al. |

FOREIGN PATENT DOCUMENTS

| | | |
|---|---|---|
| CN | 1568174 A | 1/2005 |
| CN | 101965175 A | 2/2011 |
| CN | 103458858 A | 12/2013 |
| CN | 105326670 A | 2/2016 |
| CN | 105395373 A | 3/2016 |
| CN | 105326660 B | 4/2018 |
| CN | 105395378 B | 7/2018 |
| EP | 0037318 A1 | 10/1981 |
| EP | 0077630 A1 | 4/1983 |
| EP | 1123693 A2 | 8/2001 |
| EP | 1066024 B1 | 10/2002 |
| EP | 1384467 B1 | 5/2007 |
| FR | 2593801 B1 | 5/1986 |
| GB | 849433 A1 | 9/1960 |
| GB | 1582529 A | 1/1981 |
| GB | 2177108 B | 7/1989 |
| JP | 06134227 A | 5/1994 |
| JP | H07179887 A | 11/1994 |
| JP | H07118103 A | 5/1995 |
| JP | 07258039 A | 10/1995 |
| JP | 2001181145 A | 7/2001 |
| JP | 2002104940 A | 4/2002 |
| JP | 2003530446 A | 10/2003 |
| JP | 2004262805 A | 9/2004 |
| JP | 2004292387 A | 10/2004 |
| JP | 2004292390 A | 10/2004 |
| JP | 2004307463 A | 11/2004 |
| JP | 2005022983 A | 1/2005 |
| JP | 2005187342 A | 7/2005 |
| JP | 2006063044 A | 3/2006 |
| JP | 2006525232 A | 11/2006 |
| JP | 4016238 B2 | 9/2007 |
| JP | 2007527921 A | 10/2007 |
| JP | 4069228 B2 | 1/2008 |
| JP | 4129645 B2 | 5/2008 |

(56) References Cited

FOREIGN PATENT DOCUMENTS

| | | | | |
|---|---|---|---|---|
| JP | 2008524263 | A | 7/2008 | |
| JP | 2015512248 | A | 4/2015 | |
| JP | 2016516674 | A | 6/2016 | |
| WO | 9308787 | A1 | 5/1993 | |
| WO | 9410973 | A1 | 5/1994 | |
| WO | 9625913 | A1 | 8/1996 | |
| WO | 9726854 | A1 | 7/1997 | |
| WO | 9938489 | A1 | 8/1999 | |
| WO | 0100149 | A1 | 1/2001 | |
| WO | 0105932 | A1 | 1/2001 | |
| WO | 0117492 | A1 | 3/2001 | |
| WO | 0119946 | A1 | 3/2001 | |
| WO | 0139735 | A1 | 6/2001 | |
| WO | 02076422 | A1 | 10/2002 | |
| WO | 2004020526 | A1 | 3/2004 | |
| WO | WO 2005/048959 | A1 * | 6/2005 | ............... A61K 7/00 |
| WO | 2010006866 | A1 | 1/2010 | |
| WO | 2010034736 | A1 | 4/2010 | |
| WO | 2010111266 | A2 | 9/2010 | |
| WO | 2011120799 | A1 | 10/2011 | |
| WO | 2011134832 | A2 | 11/2011 | |
| WO | 2012004126 | A2 | 1/2012 | |
| WO | WO 2012004126 | A2 * | 1/2012 | ............... A61Q 5/12 |
| WO | 2012110608 | A2 | 8/2012 | |
| WO | 2012175677 | A2 | 12/2012 | |
| WO | 20121756821 | A2 | 12/2012 | |
| WO | 2013073849 | A1 | 5/2013 | |
| WO | 2013092719 | A1 | 6/2013 | |
| WO | 2017088459 | A1 | 6/2017 | |
| WO | 2021163728 | A1 | 8/2021 | |

OTHER PUBLICATIONS

"Herbal Essence Shampoo", Mintel, dated Jun. 1, 2014, 2 pages.
"Polyelectrolyte-Micelle—Coacervation—Effect of coacervate on the properties of shampoo", Yoshiko Kiwatari et al., J. Soc. Cosmet. Chem. Japan, vol. 38, No. 3, 2004, pp. 211-219.
1—Eccleston, G.M., Application of Emulsion Stability Theories to Mobile and Semisolid o/w Emulsions, Cosmetics Magazine, vol. 101, 1986, 18 pages.
2—Eccleston, G.M., Application of Emulsion Theory to Complex and Real Systems, International Journal of Cosmetic Science, 1985, 18 pages.
3—Eccleston, G.M., Formulating Cosmetic Emulsions, Cosmetics Magazine, vol. 112, 1997, 6 pages.
4—Eccleston, G.M., Functions of Mixed Emulsifiers and Emulsifying Waxes in Dermatological Lotions and Creams, Colloids and Surfaces, vol. 123, 1997, 14 pages.
5—Eccleston, G.M., Microstructural Changes During Storage of Cetostearyl Alcohol/ Polyoxyethylene Alkyl Ether Surfactants, University of Strathclyde, 1988, 20 pages.
6—Eccleston, G.M., Multiple Phase Oil and Water Emulsions, Journal of Cosmetic Chemists, 1990, 22 pages.
7—Eccleston, G.M., Structure and Rheology of Semisolid o/w Creams Containing Cetyl Alcohol/Non-ionic Surfactant Mixed Emulsifier and Different Polymers, International Journal of Cosmetic Science, 2004, 7 pages.
8—Eccleston, G.M., Synchrotron X-ray Investigations into the Lamellar Gel Phase Formed in Creams Prepared with Fatty Alcohols, International Journal of Pharmaceuticals, 2000, 13 pages.
9—Eccleston, G.M., The Influence of Fatty Alcohols on the Structure and Stability of Creams Preapred with Fatty Alcohols, International Journal of Cosmetic Science, 1982, 9 pages.
All Office Actions; U.S. Appl. No. 16/907,711, filed Jun. 22, 2020.
All Office Actions; U.S. Appl. No. 15/635,633, filed Jun. 28, 2017.
All Office Actions; U.S. Appl. No. 15/703,046, filed Sep. 13, 2017.
All Office Actions; U.S. Appl. No. 15/728,663, filed Oct. 10, 2017.
All Office Actions; U.S. Appl. No. 16/713,142, filed Dec. 13, 2019.
All Office Actions; U.S. Appl. No. 16/902,629, filed Jun. 16, 2020.
All Office Actions; U.S. Appl. No. 16/432,371, filed Jun. 5, 2019.
All Office Actions; U.S. Appl. No. 17/174,427, filed Feb. 12, 2021.
All Office Actions; U.S. Appl. No. 17/326,910, filed May 21, 2021.
All Office Actions; U.S. Appl. No. 17/327,972, filed May 24, 2021.
Barry & Rowe, The Characterization by Small Angle X-Ray Scattering of a Gel with a Lamellar Structure, International Journal of Pharmaceuticals, 1989, 2 pages.
Barry & Saunders, Kinetics of Structure Build-up in Self Bodied Emulsions Stabalized by Mixed Emulsifiers, Journal of Colloid Science, vol. 41, 1972, 12 pages.
Barry, B.W., Structure and Rheology of Emulsions Stabalized by Mixed Emulsifiers, British Society of Rheology, 1970, 12 pages.
Benton et al, Phase Behavior and Network Formation in a Cationic Surfactant-Fatty Alcohol System, JAOCS, vol. 64, 1987, 12 pages.
Burgess, J.D., Practical Analysis of Complex Coacervate Systems, Journal of Colloid Science, vol. 140, 1990, 10 pages.
CTFA Cosmetic Ingredient Dictionary, 1982, 3rd Edition, The Cosmetic, Toiletry & Fragrance Association, Inc., Washington, DC (book not included).
Database WPI Week 201634Thomson Scientific, London, GB;AN 2016-184949XP002798128,& CN 105 395 373 A (Cuongqing Pellets Coltd) Mar. 16, 2016 (Mar. 16, 2016)abstract, 3 pages.
Database WPI Week 201644Thomson Scientific, London, GB;AN 2016-14284BXP002798127,& CN 105 326 660 A (Chongqjng Pellets Colid) Feb. 17, 2016 (Feb. 17, 2016)abstract, 3 pages.
Encyclopedia of Polymer Science and Engineering, John Wiley & Sons, vol. 15, 1989 (book not included).
Griffin, W.C., Calculation of HLB Values of Non-Ionic Surfactants, Journal of the Society of Cosmetic Chemists; 1954. Vol. 5, pp. 249-235.
INCi: Ricinus Communis (Castor) Seed Oil, 3 pages.
Korhonen et al, Rheological Properties of Three Component Creams Containing Sorbitan Monoesters as Surfactants, International Journal of Pharmaceuticals, 2002, 2 pages.
Louden et al, A Preliminary Examination of the Structure of Gels and Emulsions Containing Cetostearyl Alcohol, International Journal of Pharmaceuticals, 1985, 2 pages.
McCutcheon, Emulsifiers and Detergents, MC Pub Company, 1989 (book not included).
Meirleir Niels De et al., "The rheological properties of hydrogenated castor oil crystals", Colloid & Polymer Science, Springer Verlag, Heidelberg, DE, vol. 292, No. 10, Jun. 12, 2014, pp. 2539-2547.
Momentive SFE839 product brochure, URL Link: https://www.momentive.com/products/showtechnicaldatasheet.aspx?id=14443, 4 pages, available Sep. 2008; accessed Jul. 17, 2015.
Noll, W., Chemistry and Technology of Silicones, Academic Press, 1968 (book not included).
Patel et al, Properties of Cetrimide / Cetostearyl Alcohol Ternary Gels; Preparation Effects, International Journal of Pharmaceuticals, 1985, 2 pages.
Savic et al, Colloidal Microstructure of Binary Systems and Model Creams Stablized with an Alkylpolyglucoside Emulsifier, Colloid Polymer Science, vol. 283, 2004, 13 pages.
Saxton, C., Antiplaque Effects and Mode of Action of a Combination of Zinc Citrate and a Nonionic Antimicrobial Agent, Scandinavian Journal, vol. 96, 1988, 7 pages.
Suzuki et al, Secondary Droplet Emulsion: Mechanism & Effects of Liquid Crystal Formation in o/w Emulsion, Journal of Dispersion Science, 1984, 24 pages.
Unpublished U.S. Appl. No. 17/174,427, filed Feb. 12, 2021, to Stefano Bartolucci et al.
Unpublished U.S. Appl. No. 17/184,814, filed Feb. 25, 2021, to Mark Anthony Brown et al.
Unpublished U.S. Appl. No. 17/326,910, filed May 21, 2021, to Howard David Hutton.
Unpublished U.S. Appl. No. 17/327,972, filed May 24, 2021, to Howard David Hutton.
Van Cutsem, Journal of the American Academy of Dermatology, XP-002288119, 1998, 2 pages.
Van Oss, C.J., Coacervation, Complex Coacervation and Flocculation, Journal of Dispersion Science, vol. 9, 1989, 14 pages.

(56) References Cited

OTHER PUBLICATIONS

Yoon et al, A Study of Gel Structure in the Nonionic Surfactant / Cetostearyl Alcohol / Water Ternary Systems by Differential Scanning Calorimeter, Journal of Dispersion Science, Year 1999, 20 pages.
De Meirleir et al. "Journal of Crystal Growth" 2013; 383: 51-56. (Year: 2013).
PCT Search Report and Written Opinion for PCT/US2022/014825 dated May 13, 2022,15 pages.

* cited by examiner

MULTI-PHASE SHAMPOO COMPOSITION WITH AN AESTHETIC DESIGN

FIELD OF THE INVENTION

The present invention relates to a container with a stable multiphase shampoo composition with an aesthetic design, specifically a multiphase composition with a cleansing phase containing a detersive surfactant and a discrete benefit phase.

BACKGROUND OF THE INVENTION

Some consumers want a shampoo composition that effectively cleans the hair, while also providing excellent conditioning, which can include good wet and dry feel, while also having a striking appearance on the store shelf and/or webpage/app.

Today, there are clear shampoos that can signal superior cleaning but generally do not appear to provide excellent conditioning and creamy shampoos that can signal excellent conditioning but generally do not appear to provide excellent cleaning. Consequently, there is consumer interest in a multiphase shampoo with stable discrete phases including a cleansing phase and a benefit phase, which can provide hair and scalp benefits including superior conditioning.

However, it can difficult to maintain discrete phases in a shampoo composition throughout the shelf life of the shampoo composition, which can include shipping, handling, and storage at home, storage facility, and/or store shelves, and repeated dispensing. Shampoo compositions, especially those that are known to provide good conditioning, generally contain charged ingredients including surfactants and polymers that can interact with each other and/or other formulation ingredients, which can diminish the shampoo's rheology, stability, efficacy, and/or user experience. These issues are compounded when the benefit phase forms an aesthetic design because even slight phase disruption or conversion will be noticeable to consumers and instead of having a striking appearance that connotates quality, the product will appear mediocre.

Therefore, there is a need for stable multiphase shampoo composition that delivers excellent cleansing and conditioning where the phases form an eye-catching aesthetic design.

SUMMARY OF THE INVENTION

A container configured to hold a multiphase shampoo composition comprising: (a) a cleansing phase comprising a detersive surfactant and an aqueous carrier; (b) a benefit phase comprising a gel network comprising: (i) a fatty alcohol; (ii) a secondary surfactant selected from the group consisting of anionic, amphoteric, zwitterionic, and combinations thereof; wherein the cleansing phase and the benefit phase are visually discrete phases, in physical contact, and form an aesthetic design suspended across at least a portion of the container; wherein the cleansing phase and the benefit phase are stable.

A container configured to hold a multiphase shampoo composition comprising: (a) a cleansing phase comprising a detersive surfactant; (b) a benefit phase comprising a gel network comprising: (i) a fatty alcohol; (ii) a secondary surfactant selected from the group consisting of anionic, amphoteric, zwitterionic, cationic, and combinations thereof; (iii) a cationic deposition polymer; wherein the cleansing phase and the benefit phase are visually discrete phases, in physical contact, and form an aesthetic design suspended across at least a portion of the container; wherein the cleansing phase and the benefit phase are stable.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Figure 1:
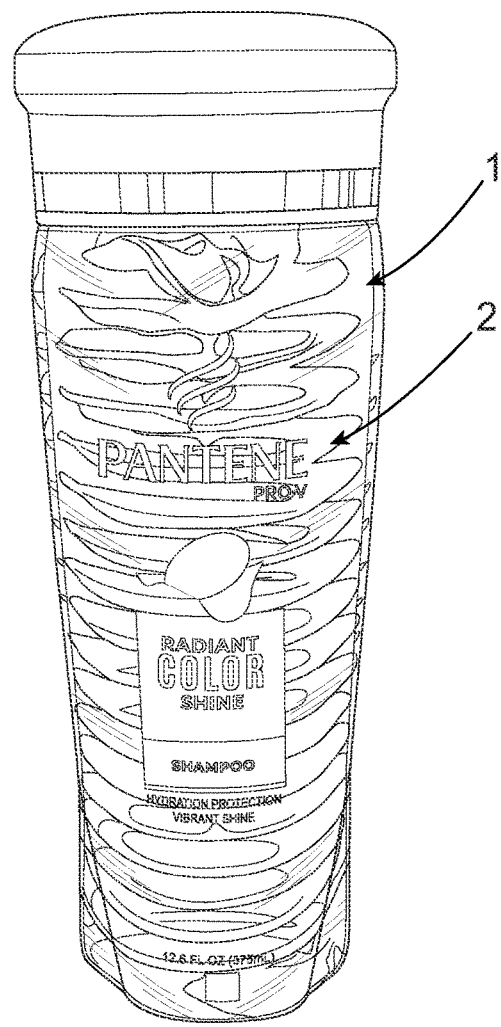
FIG. 1 is a photograph of a bottle containing a liquid shampoo composition with an aesthetic design suspended therein.
Figure 2:
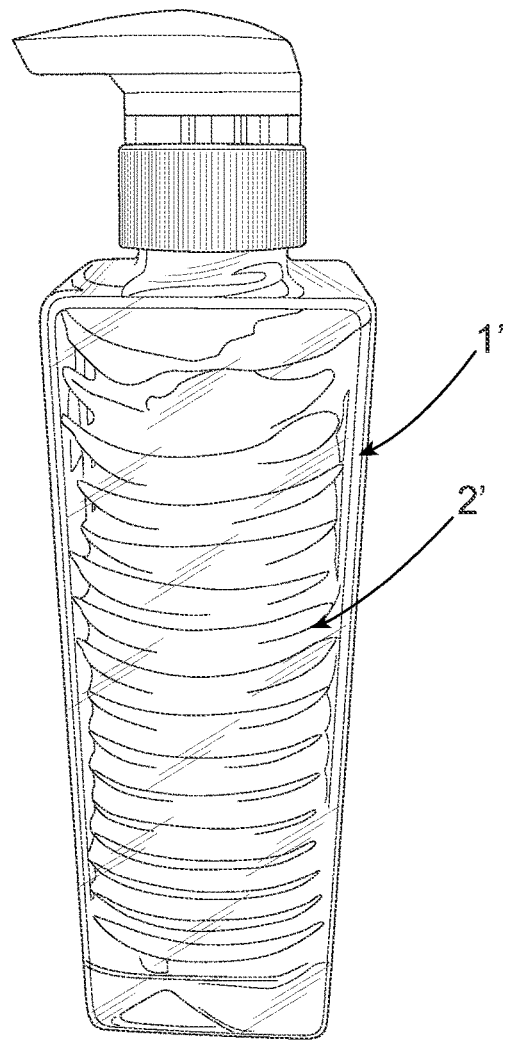
FIG. 2 is a photograph of a bottle with a pump containing a liquid shampoo composition with an aesthetic design suspended therein.

Some consumers want a shampoo composition that effectively cleans the hair while providing additional consumer benefits, such as improved wet and dry feel that can be provided by conditioning ingredients, and has a striking appearance at the store shelf and/or webpage/app. FIGS. 1 and 2 are photographs of multiphase shampoo compositions that have an aesthetic design, specifically a swirl, suspended throughout. In FIGS. 1 and 2, the two-phases are stable, discrete, and packaged in physical contact with each other. The two-phases can include cleansing phase 1, 1' and benefit phase 2, 2'.

The cleansing phase can contain a surfactant system that can include one or more detersive surfactants and a structurant. In some examples, the cleansing phase can be visibly clear with a light transmission greater than 60%, alternatively greater than 80% as measured by the Light Transmittance Method described hereafter. In other examples, the cleansing phase can appear hazy, cloudy, or even opaque. The cleansing phase can be colored, colorless, or combinations thereof.

The benefit phase can be opaque or translucent and can be suspended across the entire shampoo composition or one or more portions of the shampoo composition. The benefit phase can help the shampoo appear more conditioning without sacrificing the clarity of the cleansing phase while also providing a shampoo composition that appears different and exciting. The benefit phase can contain a gel network, which refers to a lamellar or vesicular solid crystalline phase that can contain at least one fatty alcohol, at least one surfactant, and water and/or other suitable solvents. The benefit phase can be uniform, non-uniform, or a combination thereof. The benefit phase can be any suitable shape(s) to form an aesthetic design including regular and/or irregular patterns including swirls, as show in FIGS. 1 and 2. The shape can form an aesthetic design that resembles the following non-limiting examples: bubbles, stripes, cross-hatching, zig-zag, floral, petal, herringbone, marbled, rectilinear, interrupted stripes, checked, mottled, veined, clustered, speckled, spotted, ribbons, helical, swirled, arrayed, variegated, waved, spiral, twisted, curved, streaks, laced, basket weaved, sinusoidal including but not limited to meander, and combinations thereof.

In addition to a gel network, the benefit phase can contain additional ingredients, including ingredients that could make the cleansing phase cloudy or opaque such as conditioning ingredients (e.g. cationic deposition polymer, silicones with an average particle size greater than 30 nm, crosslinked silicone elastomers), anti-dandruff actives (e.g. zinc pyrithione), aesthetic ingredients (e.g. mica), and combinations thereof. The additional ingredients can be carefully selected (e.g. the ingredient may not have too high a salt concentration) because it may disrupt the gel networks, causing the gel network structure to collapse, forcing the solvent out, which can destroy the aesthetic pattern and make the shampoo composition appear less effective.

The proper rheology, which can include viscosity, yield stress and/or shear stress, of the cleansing phase and the benefit phase can be balanced so the product is consumer acceptable, while maintaining suspended discrete stable phases. The cleansing phase can have a yield stress, Herschel-Bulkley @ shear rate $10^{-2}$ to $10^{-4}$ Pa of from about 0.01 to about 20 Pa, alternatively from about 0.01 to about 10 Pa, alternatively from about 0.01 to about 5 dPa. The yield stress is measured at 26.7° C. by flow sweep at a shear rate 100 to 1.0e-4 1/s using Discovery Hybrid Rheometer (DHR-3) available from TA Instruments. To apply the Hershel-Bulkley model, the TA software to fit the model in the log space at a shear rate from $10^{-2}$ to $10^{-4}$ $s^{-1}$ is used. The geometry used to measure the yield stress and viscosity of the cleansing phase is a 60 mm 2° aluminum cone (with a Peltier steel plate). The geometry should be run at the gap specified by the manufacturer for the geometry. Trimming the sample during the initial conditioning step in step 1 is recommended to ensure data integrity and reproducibility. Torque map the geometry prior to running the yield stress or shear stress methods when the instrument+geometry is out of calibration. The version of Trios software used to generate the rheology data herein is TRIOS 5.1.1

The cleansing phase and/or the benefit phase can have a viscosity at @ 2 s–1 Pa·s of from about 0.01 to about 15. The cleansing phase can have a viscosity @ 100 s–1 Pa·s of from about 0.1 to about 4 Pa·s, alternatively from about 0.1 to about 2 Pa·s, alternatively from about 0.1 to about 1 Pa·s.

The benefit phase can have a shear stress of about 100 Pa to about 300 Pa at a shear rate of 950 $s^{-1}$, alternatively 130 Pa to about 250 Pa at a shear rate of 950 $s^{-1}$, and alternatively about 160 Pa to about 225 Pa at a shear rate of 950 $s^{-1}$. The shear stress is measured at 25° C. by flow ramp at an initial shear rate 0.1 to final 1100 1/s using Discovery Hybrid Rheometer (DHR-3) available from TA Instruments. The geometry used to measure the yields and viscosity of the cleansing phase is a 60 mm 2° aluminum cone (with a Peltier steel plate).

The weight ratio of cleansing phase to benefit phase can be from about 1:4 to about 99:1, alternatively from about 1:1 to about 98:2, alternatively about 3:1 to about 97:3, alternatively from about 4:1 to about 95:5, alternatively from about 4:1 to about 20:1, alternatively from about 4:1 to about 10:1, alternatively from about 4:1 to about 9:1, alternatively from about 4:1 to about 6:1.

In some examples, the shampoo composition can be dispensed from a pump bottle and the ratio of cleansing phase to benefit phase can vary by less than 20% each pump, alternatively less than 15% each pump, and alternatively less than 10% each pump when dispensing the first ⅔ of the bottle contents, alternatively the first 80%, and alternatively the first 90%.

The shampoo composition can provide a mean final rinse friction less than 2000 gf, alternatively less than 1750 gf, alternatively less than 1700 gf, alternatively less than 1650 gf, and alternatively less than 1600 gf when dispensing from 10% to 55% by volume. The mean final rinse friction can be determined using the Hair Wet Feel Friction Measurement method described herein.

The shampoo composition can be sold, stored, and dispensed from a bottle. The bottle can be transparent or translucent so the user can see the design suspended in the product from the exterior of bottle. Alternatively, the bottle can be opaque and can optionally have one or more transparent or opaque windows where the consumer can see the suspended design. The shampoo composition can be dispensed from the bottle by squeezing. Alternatively, the shampoo composition can be dispensed with a pump, which may be preferred in some examples because the pump may reduce disruption of the benefit phase throughout the use of the entire bottle.

The shampoo composition can be in a bottle that is substantially free of a headspace and/or visually discernable air bubbles, to help maintain the design before use. It was found that air bubbles, especially large air bubbles, and a headspace can destroy a suspended aesthetic design during shipping and handling. A headspace can be eliminated by either overfilling the bottle or using an insert that can have a snap fit with the neck of the bottle to consume the headspace volume, an example of an insert is described in patent application No. 62/977,140, hereby incorporated herein by reference.

However, it can be difficult to eliminate all the air that is trapped in the shampoo product. After filling, shampoo products can typically have about 4% air, trapped in tiny bubbles that are not visually discernable. When the shampoo is packed in a typical bottle or pump, over time, these bubbles combine into larger bubbles due to Laplace pressure. These larger bottles will ultimately rise to the headspace if the liquid beauty care product's stress is not high enough to support the density difference between air and liquid. So even if the liquid beauty care product is packed in a bottle without any visible bubbles, a headspace can form within 24 to 48 hours. Increasing the liquid beauty product yield stress can stop bubbles migrating from small to larger bubbles and to the headspace, however a product with high yield stress can have lower acceptance with consumers due to lower spreadability and difficult dispensing.

It was found that when the headspace was eliminated (e.g. either by overfilling and/or using an insert), an overcap could be screwed or snapped onto the neck of the bottle to cause a slight over-pressure, that stopped trapped bubbles from migrating without compromising yield stress of the shampoo composition. When a user is ready to dispense the shampoo composition, they can remove the overcap and pour the shampoo product into their hand, remove the overcap and insert a pump, or in some instances the overcap can have a pierceable membrane and the user can punch through the membrane with the pump's dip tube.

It was found that the aesthetic design of the packaged shampoo product can stay substantially intact following sequence number 1-5 of the ISTA® 6A Ship Test (6-Amazon.com-Over Boxing, April 2018 using the ASTM setup for all tests). As used herein, substantially intact can mean a human viewer cannot visually discern one or more large areas where the suspended design is disturbed with the unaided eye (excepting standard corrective lenses adapted to compensate for near-sightedness, farsightedness, or astigmatism, or other corrected vision) in lighting at least equal to the illumination of a standard 100-watt incandescent white light bulb at a distance of approximately 1 foot (0.30 m). In some examples, the pattern disruption can be assessed by a taking a cross section of the liquid beauty product and determining what % of the cross section is disrupted. Less than 10% of the area of the cross section can be disrupted, alternatively less than 7%, alternatively less than 5%, alternatively less than 3%, and alternatively less than 1%.

Definitions

As used herein, the term "fluid" includes liquids and gels.

As used herein, the articles including "a" and "an" when used in a claim, are understood to mean one or more of what is claimed or described.

As used herein, "comprising" means that other steps and other ingredients which do not affect the end result can be added. This term encompasses the terms "consisting of" and "consisting essentially of".

As used herein, "mixtures" is meant to include a simple combination of materials and any compounds that may result from their combination.

As used herein, "molecular weight" or "M.Wt." refers to the weight average molecular weight unless otherwise stated. Molecular weight is measured using industry standard method, gel permeation chromatography ("GPC"). The molecular weight has units of grams/mol.

As used herein, "shampoo composition" includes shampoo products such as shampoos, shampoo conditioners, conditioning shampoos, and other surfactant-based liquid compositions.

As used herein, the term "stable" means that the cleansing phase and the benefit phase appear as discrete phases that have not migrated to a human viewer with the unaided eye (excepting standard corrective lenses adapted to compensate for near-sightedness, farsightedness, or astigmatism, or other corrected vision) in lighting at least equal to the illumination of a standard 100-watt incandescent white light bulb at a distance of approximately 1 foot (0.30 m).

As used herein, "substantially free" means from about 0 wt % to about 3 wt %, alternatively from about 0 wt % to about 2 wt %, alternatively from about 0 wt % to about 1 wt %, alternatively from about 0 wt % to about 0.5 wt %, alternatively from about 0 wt % to about 0.25 wt %, alternatively from about 0 wt % to about 0.1 wt %, alternatively from about 0 wt % to about 0.05 wt %, alternatively from about 0 wt % to about 0.01 wt %, alternatively from about 0 wt % to about 0.001 wt %, and/or alternatively free of the ingredient. As used herein, "free of" means 0 wt %.

As used herein, the terms "include," "includes," and "including," are meant to be non-limiting and are understood to mean "comprise," "comprises," and "comprising," respectively.

All percentages, parts and ratios are based upon the total weight of the compositions described herein, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Cleansing Phase

The multiphase shampoo compositions can include a cleansing phase that can be present in an amount of from about 5% to about 95%, preferably from about 10% to about 90%, and more preferably from about 20% to about 80% by weight of the composition. The cleansing phase can be an aqueous phase. The cleansing phase can have a light transmission (% T) of at least 75%, alternatively at least 80%, alternatively at least 85%, alternatively at least 90%, alternatively at least 93%, and alternatively at least 95% as measured by the Light Transmittance Method described hereafter. The cleansing phase can have a light transmission from about 60% to about 100%, alternatively from about 70% to about 98%, alternatively from about 80% to about 97%, alternatively from about 85% to about 96%, and alternatively from about 90% to about 95% as measured by the Light Transmittance Method described hereafter.

In some examples, the cleansing phase can be substantially free of or free of ingredients that can cause the phase to be cloudy, hazy, or opaque including silicones or other particles with an average particle size of greater than 30 nm, a dispersed gel network phase, synthetic polymers that form liquid crystal, and/or cationic surfactant.

In other examples, the cleansing phase can include small particle silicones (i.e. silicones with an average particle size of less than or equal to 30 nm), select cationic deposition polymer, perfumes, and/or dyes.

Detersive Surfactant

The cleansing phase can contain one or more detersive surfactants. As can be appreciated, detersive surfactants provide a cleaning benefit to soiled articles such as hair, skin, and hair follicles by facilitating the removal of oil and other soils. Surfactants generally facilitate such cleaning due to their amphiphilic nature which allows for the surfactants to break up, and form micelles around, oil and other soils which can then be rinsed out, thereby removing them from the soiled article. Suitable surfactants for a shampoo composition can include anionic moieties to allow for the formation of a coacervate with a cationic polymer. Suitable detersive surfactants can be compatible with the other ingredients in the cleansing phase and the adjacent benefit phase (s). The detersive surfactant can be selected from the group consisting of anionic surfactants, amphoteric surfactants, nonionic surfactants, and mixtures thereof.

The concentration of the surfactant in the composition should be sufficient to provide the desired cleaning and lather performance The cleansing phase can contain a surfactant system at concentrations ranging from about 1% to about 50%, alternatively from about 3% to about 45%, alternatively from about 5% to about 40%, alternatively from about 7% to about 35%, alternatively from about 8% to about 30%, alternatively from about 8% to about 25%, alternatively from about 10% to about 20%, alternatively from about 11% to about 24%, and alternatively from about 12% to about 23%, by weight of the cleansing phase. The preferred pH range of the cleansing phase is from about 3 to about 10, alternatively from about 5 to about 8, and alternatively from about 5 to about 7.

The cleansing phase can contain one or more anionic surfactants at concentrations ranging from about 1% to 50%, alternatively from about 3% to about 40%, alternatively from about 5% to about 30%, alternatively from about 6% to about 25%, alternatively from about 8% to about 25%, by weight of the cleansing phase. The anionic surfactant can be the primary surfactant.

The shampoo composition comprises one or more detersive surfactants in the shampoo base. The detersive surfactant component is included in shampoo compositions to provide cleansing performance. The detersive surfactant may be selected from the group consisting of anionic, zwitterionic, amphoteric, cationic, or a combination thereof. In some examples, the detersive surfactant may be selected from the group consisting of anionic, zwitterionic, amphoteric, or a combination thereof. Such surfactants should be physically and chemically compatible with the components described herein, or should not otherwise unduly impair product stability, aesthetics or performance Particularly suitable herein is sodium laureth- n- sulfate, wherein n=1 ("SLE1S"). SLE1S enables more efficient lathering and cleaning when compared to higher mole ethoxylate equivalents, especially in a shampoo composition that contains high levels of conditioning actives.

Suitable anionic detersive surfactants include those which are known for use in hair care or other personal care shampoo compositions. The anionic detersive surfactant may be a combination of sodium lauryl sulfate and sodium laureth-n sulfate. The concentration of the anionic surfactant in the composition should be sufficient to provide the desired cleaning and lather performance, and generally range from about 5% to about 30%, alternatively from about 8% to about 30%, alternatively from about 8% to about 25%, and alternatively from about 10% to about 17%, by weight of the composition.

Additional anionic surfactants suitable for use herein include alkyl and alkyl ether sulfates of the formula $ROSO_3M$ and $RO(C_2H_4O)_xSO_3M$, wherein R is alkyl or alkenyl of from about 8 to about 18 carbon atoms, x is 1 to 10, and M is a water-soluble cation such as ammonium, sodium, potassium, and triethanolamine cation or salts of the divalent magnesium ion with two anionic surfactant anions. The alkyl ether sulfates may be made as condensation products of ethylene oxide and monohydric alcohols having from about 8 to about 24 carbon atoms. The alcohols can be derived from fats such as coconut oil, palm oil, palm kernel oil, or tallow, or can be synthetic.

Other suitable anionic surfactants include water-soluble salts of the organic, sulfonic acids of the general formula $[R^1-SO_3M]$. $R^1$ being a straight chain aliphatic hydrocarbon radical having from 13 to 17 carbon atoms, alternatively from 13 to 15 carbon atoms. M is a water soluble cation such as ammonium, sodium, potassium, and triethanolamine cation or salts of the divalent magnesium ion with two anionic surfactant anions. These materials are produced by the reaction of $SO_2$ and $O_2$ with suitable chain length normal paraffins ($C_{14}$-$C_{17}$) and are sold commercially as sodium paraffin sulfonates.

Examples of additional anionic surfactants suitable for use include, but are not limited to, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium trideceth sulfate, sodium tridecyl sulfate, sodium methyl lauroyl taurate, sodium methyl cocoyl taurate, sodium lauroyl isethionate, sodium cocoyl isethionate, sodium laurethsulfosuccinate, sodium laurylsulfosuccinate, sodium tridecyl benzene sulfonate, sodium dodecyl benzene sulfonate, and mixtures thereof.

The shampoo composition may further comprise additional surfactants for use in combination with the anionic detersive surfactant component described herein. Suitable additional surfactants include cationic and nonionic surfactants.

Non-limiting examples of other anionic, zwitterionic, amphoteric, cationic, nonionic, or optional additional surfactants suitable for use in the compositions are described in McCutcheon's, Emulsifiers and Detergents, 1989 Annual, published by M. C. Publishing Co., and U.S. Pat. Nos. 3,929,678; 2,658,072; 2,438,091; and 2,528,378.

The shampoo compositions described herein can be substantially free of sulfate-based surfactants.

The one or more additional anionic surfactants may be selected from the group consisting of isethionates, sarcosinates, sulfonates, sulfosuccinates, sulfoacetates, acyl glycinates, acyl alaninates, acyl glutamates, lactates, lactylates, glucose carboxylates, amphoacetates, taurates, phosphate esters, and mixtures thereof. In that case, alkyl is defined as a saturated or unsaturated, straight or branched alkyl chain with 7 to 17 carbon atoms, alternatively with 9 to 13 carbon atoms. In that case, acyl is defined as of formula R—C(O)—, wherein R is a saturated or unsaturated, straight or branched alkyl chain with 7 to 17 carbon atoms, alternatively with 9 to 13 carbon atoms.

Suitable isethionate surfactants can include the reaction product of fatty acids esterified with isethionic acid and neutralized with sodium hydroxide. Suitable fatty acids for isethionate surfactants can be derived from coconut oil or palm kernel oil including amides of methyl tauride. Non-limiting examples of isethionates can be selected from the group consisting of sodium lauroyl methyl isethionate, sodium cocoyl isethionate, ammonium cocoyl isethionate, sodium hydrogenated cocoyl methyl isethionate, sodium lauroyl isethionate, sodium cocoyl methyl isethionate, sodium myristoyl isethionate, sodium oleoyl isethionate, sodium oleyl methyl isethionate, sodium palm kerneloyl isethionate, sodium stearoyl methyl isethionate, and mixtures thereof.

Non-limiting examples of sarcosinates can be selected from the group consisting of sodium lauroyl sarcosinate, sodium cocoyl sarcosinate, sodium myristoyl sarcosinate, TEA-cocoyl sarcosinate, ammonium cocoyl sarcosinate, ammonium lauroyl sarcosinate, dimer dilinoleyl bis-lauroyl-glutamate/lauroylsarcosinate, disodium lauroamphodiacetate, lauroyl sarcosinate, isopropyl lauroyl sarcosinate, potassium cocoyl sarcosinate, potassium lauroyl sarcosinate, sodium cocoyl sarcosinate, sodium lauroyl sarcosinate, sodium myristoyl sarcosinate, sodium oleoyl sarcosinate, sodium palmitoyl sarcosinate, TEA-cocoyl sarcosinate, TEA-lauroyl sarcosinate, TEA-oleoyl sarcosinate, TEA-palm kernel sarcosinate, and combinations thereof.

Non-limiting examples of sulfosuccinate surfactants can include disodium N-octadecyl sulfosuccinate, disodium lauryl sulfosuccinate, diammonium lauryl sulfosuccinate, sodium lauryl sulfosuccinate, disodium laureth sulfosuccinate, tetrasodium N-(1,2-dicarboxyethyl)-N-octadecyl sulfosuccinnate, diamyl ester of sodium sulfosuccinic acid, dihexyl ester of sodium sulfosuccinic acid, dioctyl esters of sodium sulfosuccinic acid, and combinations thereof.

Non-limiting examples of sulfoacetates can include sodium lauryl sulfoacetate, ammonium lauryl sulfoacetate and combination thereof.

Non-limiting examples of acyl glycinates can include sodium cocoyl glycinate, sodium lauroyl glycinate and combination thereof.

Non-limiting example of acyl alaninates can include sodium cocoyl alaninate, sodium lauroyl alaninate, sodium N-dodecanoyl-l-alaninate and combinations thereof.

Non-limiting examples of acyl glutamates can be selected from the group consisting of sodium cocoyl glutamate, disodium cocoyl glutamate, ammonium cocoyl glutamate, diammonium cocoyl glutamate, sodium lauroyl glutamate, disodium lauroyl glutamate, sodium cocoyl hydrolyzed wheat protein glutamate, disodium cocoyl hydrolyzed wheat protein glutamate, potassium cocoyl glutamate, dipotassium cocoyl glutamate, potassium lauroyl glutamate, dipotassium lauroyl glutamate, potassium cocoyl hydrolyzed wheat protein glutamate, dipotassium cocoyl hydrolyzed wheat protein glutamate, sodium capryloyl glutamate, disodium capryloyl glutamate, potassium capryloyl glutamate, dipotassium capryloyl glutamate, sodium undecylenoyl glutamate, disodium undecylenoyl glutamate, potassium undecylenoyl glutamate, dipotassium undecylenoyl glutamate, disodium hydrogenated tallow glutamate, sodium stearoyl glutamate, disodium stearoyl glutamate, potassium stearoyl glutamate, dipotassium stearoyl glutamate, sodium myristoyl glutamate, disodium myristoyl glutamate, potassium myristoyl glutamate, dipotassium myristoyl glutamate, sodium cocoyl/hydrogenated tallow glutamate, sodium cocoyl/palmoyl/sunfloweroyl glutamate, sodium hydrogenated tallowoyl glutamate, sodium olivoyl glutamate, disodium olivoyl glutamate, sodium palmoyl glutamate, disodium palmoyl glutamate, TEA-cocoyl glutamate, TEA-hydrogenated tallowoyl glutamate, TEA-lauroyl glutamate, and mixtures thereof.

Non-limiting examples of acyl glycinates can include sodium cocoyl glycinate, sodium lauroyl glycinate and combination thereof.

Non-limiting example of lactates can include sodium lactate.

Non-limiting examples of lactylates can include sodium lauroyl lactylate, sodium cocoyl lactylate and combination thereof.

Non-limiting examples of glucose carboxylates can include sodium lauryl glucoside carboxylate, sodium cocoyl glucoside carboxylate and combinations thereof.

Non-limiting examples of alkylamphoacetates can include sodium cocoyl amphoacetate, sodium lauroyl amphoacetate and combination thereof.

Non-limiting examples of acyl taurates can include sodium methyl cocoyl taurate, sodium methyl lauroyl taurate, sodium methyl oleoyl taurate and combination thereof.

The cleansing phase can contain one or more amphoteric and/or zwitterionic and/or non-ionic co-surfactants at concentrations ranging from about 0.25% to about 50%, alternatively from about 0.5% to about 30%, alternatively about 0.75% to about 15%, alternatively from about 1% to about 13%, and alternatively from about 2% to about 10%, by weight of the cleansing phase. The co-surfactant may serve to produce faster lather, facilitate easier rinsing, and/or mitigate harshness on the keratinous tissue. The co-surfactant further may aid in producing lather having more desirable texture, volume and/or other properties.

Amphoteric surfactants suitable for use herein include, but are not limited to derivatives of aliphatic secondary and tertiary amines in which the aliphatic radical can be straight or branched chain and wherein one substituent of the aliphatic substituents contains from about 8 to about 18 carbon atoms and one contains an anionic water solubilizing group, e.g., carboxy, sulfonate, sulfate, phosphate, or phosphonate. Examples include sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378, and mixtures thereof. The amphoteric surfactants may selected from the family of betaines such as lauryolamphoacetate.

Zwitterionic surfactants suitable for use herein include, but are not limited to derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one substituent contains an anionic group, e.g., carboxy, sulfonate, sulfate, phosphate, or phosphonate. Other zwitterionic surfactants suitable for use herein include betaines, including high alkyl betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, and mixtures thereof. The sulfobetaines may include coco dimethyl sulfopropyl betaine, stearyl dimethyl sulfopropyl betaine, lauryl dimethyl sulfoethyl betaine, lauryl bis-(2-hydroxyethyl) sulfopropyl betaine and mixtures thereof. Other suitable amphoteric surfactants include amidobetaines and amidosulfobetaines, wherein the RCONH($CH_2$)$_3$ radical, wherein R is a $C_{11}$-$C_{17}$ alkyl, is attached to the nitrogen atom of the betaine.

Nonionic co-surfactants suitable for use in the composition for enhancing lather volume or texture include water soluble materials like lauryl dimethylamine oxide, cocodimethylamine oxide, cocoamidopropylamine oxide, laurylamidopropyl amine oxide, etc. or alkylpolyethoxylates like laureth-4 to laureth-7 and water insoluble components such as cocomonoethanol amide, cocodiethanol amide, lauroylmonoethanol amide, alkanoyl isopropanol amides, and fatty alcohols like cetyl alcohol and oleyl alcohol, and 2-hydroxyalkyl methyl ethers, etc.

Further suitable materials as co-surfactants herein include 1,2-alkylepoxides, 1,2-alkanediols, branched or straight chain alkyl glyceryl ethers (e.g., as disclosed in EP 1696023A1), 1,2-alkylcyclic carbonates, and 1,2-alkyl cyclicsulfites, particularly those wherein the alkyl group contains 6 to 14 carbon atoms in linear or branched configuration. Other examples include the alkyl ether alcohols derived from reacting $C_{10}$ or C12 alpha olefins with ethylene glycol (e.g., hydroxyethyl-2-decyl ether, hydroxyethyl-2-dodecyl ether), as can be made according to U.S. Pat. Nos. 5,741,948; 5,994,595; 6,346,509; and 6,417,408.

Other nonionic surfactants may be selected from the group consisting of glucose amides, alkyl polyglucosides, sucrose cocoate, sucrose laurate, alkanolamides, ethoxylated alcohols and mixtures thereof. The nonionic surfactant is selected from the group consisting of glyceryl monohydroxystearate, isosteareth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, and mixtures thereof.

The co-surfactant can be selected from the group consisting of Cocomonoethanol Amide, Cocoamidopropyl Betaine, Laurylamidopropyl Betaine, Cocobetaine, lauryl betaine, lauryl amine oxide, sodium lauryl amphoacetate; alkyl glyceryl ethers, alkyl-di-glyceryl ethers, 1,2-alkyl cyclic sulfites, 1,2-alkyl cyclic carbonates, 1,2-alkyl-epoxides, alkyl glycidylethers, and alkyl-1,3-dioxolanes, wherein the alkyl group contains 6 to 14 carbon atoms in linear or branched configuration; 1,2- alkane diols where the total carbon content is from 6 to 14 carbon atoms linear or branched, methyl-2-hydroxy-decyl ethers, hydroxyethyl-2-dodecyl ether, hydroxyethyl-2-decyl ether, and mixtures thereof.

Cationic surfactants may be derived from amines that are protonated at the pH of the formulation, e.g. bis-hydroxyethyl lauryl amine, lauryl dimethylamine, lauroyl dimethyl amidopropyl amine, cocoylamidopropyl amine, and the like. The cationic surfactants may also be derived from fatty quaternary ammonium salts such as lauryl trimethylammonium chloride and lauroylamidopropyl trimethyl ammonium chloride.

Alkylamphoacetates are suitable surfactants used in the compositions herein for improved product mildness and lather. The most commonly used alkylamphoacetates are lauroamphoacetate and cocoamphoacetate. Alkylamphoacetates can be comprised of monoacetates and diacetates. In some types of alkylamphoacetates, diacetates are impurities or unintended reaction products. However, the presence of diacetate can cause a variety of unfavorable composition characteristics when present in amounts over 15% of the alkylamphoacetates.

Suitable nonionic surfactants for use herein are those selected from the group consisting of glucose amides, alkyl polyglucosides, sucrose cocoate, sucrose laurate, alkanolamides, ethoxylated alcohols and mixtures thereof. In one embodiment the nonionic surfactant is selected from the group consisting of glyceryl monohydroxystearate, isosteareth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, and mixtures thereof.

If present, the composition may comprise a rheology modifier, wherein said rheology modifier comprises cellulosic rheology modifiers, cross-linked acrylates, cross-linked maleic anhydride co-methylvinylethers, hydrophobically modified associative polymers, or a mixture thereof.

An electrolyte, if used, can be added per se to the composition or it can be formed in situ via the counterions included in one of the raw materials. The electrolyte may include an anion comprising phosphate, chloride, sulfate or citrate and a cation comprising sodium, ammonium, potassium, magnesium or mixtures thereof. The electrolyte may be sodium chloride, ammonium chloride, sodium or ammonium sulfate. The electrolyte may be added to the composition in the amount of from about 0.1 wt % to about 15 wt % by weight, alternatively from about 1 wt % to about 6 wt % by weight, and alternatively from about 3 wt % to about 6 wt %, by weight of the composition.

Structurant

The cleansing phase can include a structurant (ex. cross-linked polyacrylate, Carbopol® Aqua SF-1 polymer, available from Lubrizol®) that can provide the high, low-shear viscosity and yield stress to maintain the stable discrete product phases in the shampoo composition overtime, which includes shipping, handling, distribution, and storage at a store, warehouse, or consumer's home shelf. The cleansing phase can include a structurant at concentrations effective for suspending a benefit phase in the cleansing phase and/or for modifying the viscosity of the composition. Such concentrations can range from about 0.05% to about 10%, alternatively from about 0.3% to about 5.0%, and alternatively from about 1.5% to about 5.0% by weight of the cleansing phase. As can be appreciated however, certain glyceride ester crystals can act as suitable structurants or suspending agents.

Suitable structurants can include anionic polymers and nonionic polymers. Useful herein are vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carragheenin, pectin, agar, quince seed (Cydonia oblonga Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid.

Other suitable structurants can include crystalline structurants which can be categorized as acyl derivatives, long chain amine oxides, and mixtures thereof. Examples of such structurants are described in U.S. Pat. No. 4,741,855, which is incorporated herein by reference. Suitable structurants include ethylene glycol esters of fatty acids having from 16 to 22 carbon atoms. The structurant can be an ethylene glycol stearates, both mono and distearate, but particularly the distearate containing less than about 7% of the mono stearate. Other suitable structurants include alkanol amides of fatty acids, having from about 16 to about 22 carbon atoms, alternatively from about 16 to about 18 carbon atoms, suitable examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters as previously described. Long chain acyl derivatives, ethylene glycol esters of long chain carboxylic acids, long chain amine oxides, and alkanol amides of long chain carboxylic acids can also be used as structurants.

Other long chain acyl derivatives suitable for use as structurants include N,N-dihydrocarbyl amido benzoic acid and soluble salts thereof (e.g., Na, K), particularly N,N-di (hydrogenated) $C_{16}$, $C_{18}$ and tallow amido benzoic acid species of this family, which are commercially available from Stepan Company (Northfield, Ill., USA).

Examples of suitable long chain amine oxides for use as structurants include alkyl dimethyl amine oxides, e.g., stearyl dimethyl amine oxide.

Other suitable structurants include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Still other suitable structurants include di(hydrogenated tallow)phthalic acid amide, and crosslinked maleic anhydride-methyl vinyl ether copolymer.

Other suitable structurants include crystallizable glyceride esters. For example, suitable glyceride esters are hydrogenated castor oils such as trihydroxystearin or dihydroxystearin. Examples of additional crystallizable glyceride esters can include the substantially pure triglyceride of 12-hydroxystearic acid. 12-hydroxystearic acid is the pure form of a fully hydrogenated triglyceride of 12-hydrox-9-cis-octadecenoic acid. As can be appreciated, many additional glyceride esters are possible. For example, variations in the hydrogenation process and natural variations in castor oil can enable the production of additional suitable glyceride esters from castor oil.

Viscosity Modifier

Viscosity modifiers can optionally be used to modify the rheology of the cleansing phase. Suitable viscosity modifiers can include Carbomers with tradenames Carbopol 934, Carbopol 940, Carbopol 950, Carbopol 980, and Carbopol 981, all available from B. F. Goodrich Company, acrylates/steareth-20 methacrylate copolymer with tradename ACRYSOL 22 available from Rohm and Hass, nonoxynyl hydroxyethylcellulose with tradename AMERCELL POLYMER HM-1500 available from Amerchol, methylcellulose with tradename BENECEL, hydroxyethyl cellulose with tradename NATROSOL, hydroxypropyl cellulose with tradename KLUCEL, cetyl hydroxyethyl cellulose with tradename POLYSURF 67, all supplied by Hercules, ethylene oxide and/or propylene oxide based polymers with tradenames CARBOWAX PEGs, POLYOX WASRs, and UCON FLUIDS, all supplied by Amerchol. Sodium chloride can also be used as a viscosity modifier. Other suitable rheology modifiers can include cross-linked acrylates, cross-linked maleic anhydride co-methylvinylethers, hydrophobically modified associative polymers, and mixtures thereof.

Benefit Phase

The benefit phase can include a gel network that can contain one or more fatty alcohols. The gel network can provide conditioning benefits. As used herein, the term "gel network" refers to a lamellar or vesicular solid crystalline phase which comprises at least one fatty alcohol as specified below, at least one secondary surfactant and/or fatty acid as specified below, and water and/or other suitable solvents. The lamellar or vesicular phase comprises bi-layers made up of a first layer comprising the fatty alcohol and/or fatty acid and the secondary surfactant and/or fatty acid and alternating with a second layer comprising the water or other suitable solvent. In another example, the gel network can include at least one fatty acid, at least one secondary surfactant, and water and/or other suitable solvents. The term "solid crystalline", as used herein, refers to the structure of the lamellar or vesicular phase which forms at a temperature below the melt transition temperature of the layer in the gel network comprising the one or more fatty alcohols.

The multiphase shampoo compositions can include benefit phase that can be present in an amount of from about 1% to about 90%, alternatively from about 2% to about 50%, alternatively from about 5% to about 40%, alternatively from about 7% to about 30%, alternatively from about 10% to about 25%, by weight of the shampoo composition. The benefit phase can have a transmission of less than 55%, alternatively less than 50%, alternatively less than 40%, alternatively less than 30%, and alternatively less than 25%, as measured by the Light Transmittance Method described hereafter. In some examples, the benefit phase can be substantially free of a structurant. In other examples, the benefit phase can be free of cationic surfactant and/or anionic surfactant.

The gel network as described herein can be prepared as a separate pre-mix, which, after being cooled, is combined with the cleansing phase as a visually discrete phase. Preparation of the gel network component is discussed in more detail below as well as in the Examples.

The cooled and pre-formed gel network component subsequently is added to the other components of the shampoo composition, including the detersive surfactant component. While not intending to be limited by theory, it is believed that incorporation of the cooled and pre-formed gel network component with the detersive surfactant and other components of the shampoo composition allows the formation of a substantially equilibrated lamellar dispersion ("ELD") in the final shampoo composition. The ELD is a dispersed lamellar or vesicular phase resulting from the pre-formed gel network component substantially equilibrating with the detersive surfactants, water, and other optional components, such as salts, which may be present in the shampoo composition. This equilibration occurs upon incorporation of the pre-formed gel network component with the other components of the shampoo composition and is effectively complete within about 24 hours after making Shampoo compositions in which the ELD is formed provide hair with improved wet and dry conditioning benefits.

For purposes of clarification, as used herein, the term "ELD" refers to the same component of the shampoo compositions of the present invention as the phrase "gel network phase".

The presence of the gel network in the pre-mix and in the final shampoo composition in the form of the ELD can be confirmed by means known to one of skill in the art, such as X-ray analysis, optical microscopy, electron microscopy, and differential scanning calorimetry. A method of differential scanning calorimetry is described below. For methods of X-ray analysis, see U.S. 2006/0024256 A1.

The scale size of the gel network phase in the shampoo composition (i.e., the ELD) can range from about 10 nm to about 500 nm. The scale size of the gel network phase in the shampoo composition can range from about 0.5 µm to about 10 µm. Alternatively, the scale size of the gel network phase in the shampoo composition can range from about 10 µm to about 150 µm.

The scale size distribution of the gel network phase in the shampoo composition may be measured with a laser light scattering technique, using a Horiba model LA 910 Laser Scattering Particle Size Distribution Analyzer (Horiba Instruments, Inc. Irvine Calif., USA). The scale size distribution in a shampoo composition of the present invention may be measured by combining 1.75 g of the shampoo composition with 30 mL of 3% $NH_4Cl$, 20 mL of 2% $Na_2HPO_4.7H_2O$, and 10 mL of 1% laureth-7 to form a mixture. This mixture is then stirred for 5 minutes. As appropriate for the individual Horiba instrument being used, samples in the range of 1 to 40 mL are taken and then injected into the Horiba instrument, which contains 75 mL of 3% $NH_4Cl$, 50 mL of 2% $Na_2HPO_4.7H_2O$, and 25 mL of 1% laureth-7, until the Horiba instrument reading is between 88-92% T, which is needed for the scale size measurement. Once this is achieved, a measurement is taken after 2 minutes of circulation through the Horiba instrument to provide the scale size measurement. A subsequent measurement is taken using a sample of the shampoo composition which has been heated above the melt transition temperature of all fatty materials present in the shampoo composition, such that the gel network component is melted. This subsequent measurement allows a scale size distribution to be taken of all of the remaining materials in the shampoo, which then can be compared to the scale size distribution of the first sample and assist in the analysis.

Fatty Alcohol

The gel network component of the present invention can comprise at least one fatty alcohol. Individual fatty alcohol compounds or combinations of two or more different fatty alcohol compounds may be selected.

Fatty alcohols suitable for use in the present invention can include those having from about 16 to about 70 carbon atoms, alternatively from about 16 to about 60 carbon atoms, alternatively from about 16 to about 50 carbon atoms, alternatively from about 16 to about 40 carbon atoms, and alternativley from about 16 to about 22 carbon atoms. These fatty alcohols may be straight or branched chain alcohols and may be saturated or unsaturated. Non-limiting examples of suitable fatty alcohols include stearyl alcohol, arachidyl alcohol, behenyl alcohol, C21 fatty alcohol (1-heneicosanol), C23 fatty alcohol (1-tricosanol), C24 fatty alcohol (lignoceryl alcohol, 1-tetracosanol), C26 fatty alcohol (1-hexacosanol), C28 fatty alcohol (1-octacosanol), C30 fatty alcohol (1-triacontanol), C20-40 alcohols (e.g., Performacol 350 and 425 Alcohols, available from New Phase Technologies), C30-50 alcohols (e.g., Performacol 550 Alcohol), C40-60 alcohols (e.g., Performacol 700 Alcohol), cetyl alcohol, and mixtures thereof.

Mixtures of different fatty alcohols comprising one or more fatty alcohols having from about 16 to about 70 carbon atoms may also comprise some amount of one or more fatty alcohols or other fatty amphiphiles which have less than about 16 carbon atoms or greater than about 70 carbon atoms and still be considered to be within the scope of the present invention, provided that the resulting gel network phase can have a melt transition temperature of at least about 25° C., alternatively at least about 28° C., alternatively at least about 31° C., alternatively at least about 34° C., and alternatively at least about 37° C.

Such fatty alcohols suitable for use in the present invention may be of natural or vegetable origin, or they may be of synthetic origin.

The benefit phase may include fatty alcohol as part of the gel network phase in an amount of at least about 2.8%, alternatively from about 2.8% to about 25%, alternatively from about 4% to about 23%, alternatively from about 5% to about 20%, alternatively from about 6% to about 18%, alternatively from about 7% to about 15%, alternatively from about 8% to about 13%, by weight of the benefit phase.

In an embodiment of the present invention, the weight ratio of the fatty alcohol to the secondary surfactant in the gel network component is greater than about 1:9, alternatively from about 1:5 to about 100:1, and alternatively from about 1:1 to about 50:1.

Secondary Surfactant

The gel network component of the present invention may also comprise a secondary surfactant. As used herein, "secondary surfactant" refers to one or more surfactants which are combined with the fatty alcohol and water to form the gel network of the present invention as a pre-mix separate from the other components of the shampoo composition. The secondary surfactant is separate from and in addition to the detersive surfactant component of the cleansing phase. However, the secondary surfactant may be the same or different type of surfactant or surfactants as that or those selected for the detersive surfactant component described above.

The benefit phase of the present invention comprise secondary surfactant as part of the pre-formed gel network phase in an amount from about 0.01% to about 15%, alternatively, about 0.5% to about 12%, alternatively from about 0.7% to about 10%, and alternatively from about 1% to about 6%, by weight of the benefit phase.

Suitable secondary surfactants include anionic, zwitterionic, amphoteric, cationic, and nonionic surfactants. The secondary surfactant may be selected from anionic, cationic, and nonionic surfactants, and mixtures thereof. For additional discussion of secondary surfactants which are suitable for use in the present invention, see U.S. 2006/0024256 A1.

Additionally, certain secondary surfactants which have a hydrophobic tail group with a chain length of from about 16 to about 22 carbon atoms. For such secondary surfactants, the hydrophobic tail group may be alkyl, alkenyl (containing up to 3 double bonds), alkyl aromatic, or branched alkyl. the secondary surfactant may be present in the gel network component relative to the fatty alcohol at a weight ratio from about 1:5 to about 5:1. SLE1S may be particularly useful as SLE1S is a very efficient surfactant which foams well. In a shampoo composition with high levels of conditioning actives, SLE1S may further provide enhanced lather and cleaning.

Mixtures of more than one surfactant of the above specified types may be used for the secondary surfactant of the present invention.

Examples of gel network premixes may be found in U.S. Pat. No. 8,361,448 and US Pub. No. 2017/0367955, which are hereby incorporated by reference.

Fatty Acid

Non-limiting examples of suitable fatty acids, which can be combined with either the fatty alcohol or the secondary surfactant to form a gel network, can include unsaturated and/or branched long chain ($C_8$-$C_{24}$) liquid fatty acids or ester derivative thereof; unsaturated and/or branched long chain liquid alcohol or ether derivatives thereof, and mixtures thereof. The fatty acid can include short chain saturated fatty acids such as capric acid and caprylic acid. Without being limited by theory, it is believed that the unsaturated part of the fatty acid of alcohol or the branched part of the fatty acid or alcohol acts to "disorder" the surfactant hydrophobic chains and induce formation of lamellar phase. Examples of suitable liquid fatty acids can include oleic acid, isostearic acid, linoleic acid, linolenic acid, ricinoleic acid, elaidic acid, arichidonic acid, myristoleic acid, palmitoleic acid, and mixtures thereof. Examples of suitable ester derivatives can include propylene glycol isostearate, propylene glycol oleate, glyceryl isostearate, glyceryl oleate, polyglyceryl diisostearate and mixtures thereof. Examples of alcohols can include oleyl alcohol and isostearyl alcohol. Examples of ether derivatives can include isosteareth or oleth carboxylic acid; or isosteareth or oleth alcohol. The structuring agent may be defined as having melting point below about 25° C.

Cationic Deposition Polymer

The benefit phase and/or cleansing phase may contain a cationic deposition polymer. In some examples, the cleansing phase can be substantially free of any cationic deposition polymer or level thereof that could make the composition appear hazy or cloudy to a human viewer with the unaided eye (e.g. Polyquaternium-6). The cationic deposition polymer can be added at a level from about 0.1% to about 15%, preferably from 0.5% to about 8%, more preferably from about 1% to about 5%, by weight of the benefit phase, cleansing phase, or shampoo composition of the cationic deposition polymer.

A shampoo composition can include a cationic polymer to allow formation of a coacervate. As can be appreciated, the cationic charge of a cationic polymer can interact with an anionic charge of a surfactant to form the coacervate. Suitable cationic polymers can include: (a) a cationic guar polymer, (b) a cationic non-guar galactomannan polymer, (c) a cationic starch polymer, (d) a cationic copolymer of acrylamide monomers and cationic monomers, (e) a synthetic, non-crosslinked, cationic polymer, which may or may not form lyotropic liquid crystals upon combination with the detersive surfactant, (f) cationic synthetic homopolymers, (g) a cationic cellulose polymer, and (h) combinations thereof. In certain examples, more than one cationic polymer can be included. The cationic polymer can be selected from guar hydroxypropyltrimonium chloride, Polyquaterium 10, Polyquaternium 6, and combinations thereof.

Cationic polymers can have cationic charge densities of about 0.9 meq/g or more, about 1.2 meq/g or more, and about 1.5 meq/g or more. However, cationic charge density can also be about 7 meq/g or less and alternatively about 5 meq/g or less. The charge densities can be measured at the pH of intended use of the shampoo composition. (e.g., at about pH 3 to about pH 9; or about pH 4 to about pH 8). The average molecular weight of cationic polymers can generally be between about 10,000 and 10 million, between about 50,000 and about 5 million, and between about 100,000 and about 3 million, and between about 300,000 and about 3 million and between about 100,000 and about 2.5 million. Low molecular weight cationic polymers can be used. Low molecular weight cationic polymers can have greater translucency in the liquid carrier of a shampoo composition. The cationic polymer can be a single type, such as the cationic guar polymer guar hydroxypropyltrimonium chloride having a weight average molecular weight of about 2.5 million g/mol or less, and the shampoo composition can have an additional cationic polymer of the same or different types.

Cationic Guar Polymer

The cationic polymer can be a cationic guar polymer, which is a cationically substituted galactomannan (guar) gum derivative. Suitable guar gums for guar gum derivatives can be obtained as a naturally occurring material from the seeds of the guar plant. As can be appreciated, the guar molecule is a straight chain mannan which is branched at regular intervals with single membered galactose units on alternative mannose units. The mannose units are linked to each other by means of β(1-4) glycosidic linkages. The galactose branching arises by way of an α(1-6) linkage. Cationic derivatives of the guar gums can be obtained through reactions between the hydroxyl groups of the polygalactomannan and reactive quaternary ammonium compounds. The degree of substitution of the cationic groups onto the guar structure can be sufficient to provide the requisite cationic charge density described above.

A cationic guar polymer can have a weight average molecular weight ("M.Wt.") of less than about 3 million g/mol, and can have a charge density from about 0.05 meq/g to about 2.5 meq/g. Alternatively, the cationic guar polymer can have a weight average M.Wt. of less than 1.5 million g/mol, from about 150 thousand g/mol to about 1.5 million g/mol, from about 200 thousand g/mol to about 1.5 million g/mol, from about 300 thousand g/mol to about 1.5 million g/mol, and from about 700,000 thousand g/mol to about 1.5 million g/mol. The cationic guar polymer can have a charge density from about 0.2 meq/g to about 2.2 meq/g, from about 0.3 meq/g to about 2.0 meq/g, from about 0.4 meq/g to about 1.8 meq/g; and from about 0.5 meq/g to about 1.7 meq/g.

A cationic guar polymer can have a weight average M.Wt. of less than about 1 million g/mol, and can have a charge density from about 0.1 meq/g to about 2.5 meq/g. A cationic guar polymer can have a weight average M.Wt. of less than 900 thousand g/mol, from about 150 thousand to about 800 thousand g/mol, from about 200 thousand g/mol to about 700 thousand g/mol, from about 300 thousand to about 700 thousand g/mol, from about 400 thousand to about 600 thousand g/mol, from about 150 thousand g/mol to about 800 thousand g/mol, from about 200 thousand g/mol to about 700 thousand g/mol, from about 300 thousand g/mol to about 700 thousand g/mol, and from about 400 thousand g/mol to about 600 thousand g/mol. A cationic guar polymer has a charge density from about 0.2 meq/g to about 2.2 meq/g, from about 0.3 meq/g to about 2.0 meq/g, from about 0.4 meq/g to about 1.8 meq/g; and from about 0.5 meq/g to about 1.5 meq/g.

A shampoo composition can include from about 0.01% to less than about 0.7%, by weight of the shampoo composition of a cationic guar polymer, from about 0.04% to about 0.55%, by weight, from about 0.08% to about 0.5%, by weight, from about 0.16% to about 0.5%, by weight, from about 0.2% to about 0.5%, by weight, from about 0.3% to about 0.5%, by weight, and from about 0.4% to about 0.5%, by weight.

The cationic guar polymer can be formed from quaternary ammonium compounds which conform to general Formula II:

Formula II

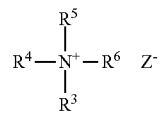

wherein where $R^3$, $R^4$ and $R^5$ are methyl or ethyl groups; and $R^6$ is either an epoxyalkyl group of the general Formula III:

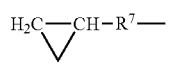

Formula III or $R^6$ is a halohydrin group of the general Formula IV:

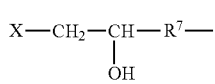

Formula IV wherein $R^7$ is a $C_1$ to $C_3$ alkylene; X is chlorine or bromine, and Z is an anion such as Cl-, Br-, I- or $HSO_4$-.

Suitable cationic guar polymers can conform to the general formula V:

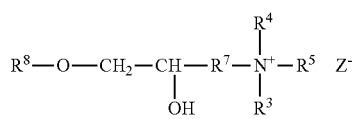

Formula V wherein $R^8$ is guar gum; and wherein $R^4$, $R^5$, $R^6$ and $R^7$ are as defined above; and wherein Z is a halogen. Suitable cationic guar polymers can conform to Formula VI:

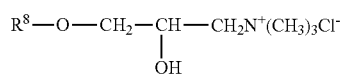

Formula VI wherein $R^8$ is guar gum.

Suitable cationic guar polymers can also include cationic guar gum derivatives, such as guar hydroxypropyltrimonium chloride. Suitable examples of guar hydroxypropyltrimonium chlorides can include the Jaguar® series commercially available from Solvay S.A., Hi-Care Series from Rhodia, and N-Hance and AquaCat from Ashland Inc. Jaguar® C-500 has a charge density of 0.8 meq/g and a M.Wt. of 500,000 g/mole; Jaguar Optima has a cationic charge density of about 1.25 meg/g and a M.Wt. of about 500,000 g/moles; Jaguar® C-17 has a cationic charge density of about 0.6 meq/g and a M.Wt. of about 2.2 million g/mol; Jaguar® and a cationic charge density of about 0.8 meq/g; Hi-Care 1000 has a charge density of about 0.7 meq/g and a M.Wt. of about 600,000 g/mole; N-Hance 3269 and N-Hance 3270, have a charge density of about 0.7 meq/g and a M.Wt. of about 425,000 g/mole; N-Hance 3196 has a charge density of about 0.8 meq/g and a M.Wt. of about 1,100,000 g/ mole; and AquaCat CG518 has a charge density of about 0.9 meq/g and a M.Wt. of about 50,000 g/mole. N-Hance BF-13 and N-Hance BF-17 are borate (boron) free guar polymers. N-Hance BF-13 has a charge density of about 1.1 meq/g and M.W.t of about 800,000 and N-Hance BF-17 has a charge density of about 1.7 meq/g and M.W.t of about 800,000. BF-17 has a charge density of about 1.7 meq/g and M.W.t of about 800,000. BF-17 has a charge density of about 1.7 meq/g and M.W.t of about 800,000. BF-17 has a charge density of about 1.7 meq/g and M.W.t of about 800,000. BF-17 has a charge density of about 1.7 meq/g and M.W.t of about 800,000.

Cationic Non-Guar Galactomannan Polymer

The cationic polymer can be a galactomannan polymer derivative. Suitable galactomannan polymer can have a mannose to galactose ratio of greater than 2:1 on a monomer to monomer basis and can be a cationic galactomannan polymer derivative or an amphoteric galactomannan polymer derivative having a net positive charge. As used herein, the term "cationic galactomannan" refers to a galactomannan polymer to which a cationic group is added. The term "amphoteric galactomannan" refers to a galactomannan polymer to which a cationic group and an anionic group are added such that the polymer has a net positive charge.

Galactomannan polymers can be present in the endosperm of seeds of the Leguminosae family Galactomannan polymers are made up of a combination of mannose monomers and galactose monomers. The galactomannan molecule is a straight chain mannan branched at regular intervals with single membered galactose units on specific mannose units. The mannose units are linked to each other by means of β(1-4) glycosidic linkages. The galactose branching arises by way of an α(1-6) linkage. The ratio of mannose monomers to galactose monomers varies according to the species of the plant and can be affected by climate. Non Guar Galactomannan polymer derivatives can have a ratio of mannose to galactose of greater than 2:1 on a monomer to monomer basis. Suitable ratios of mannose to galactose can also be greater than 3:1 or greater than 4:1. Analysis of mannose to galactose ratios is well known in the art and is typically based on the measurement of the galactose content.

The gum for use in preparing the non-guar galactomannan polymer derivatives can be obtained from naturally occurring materials such as seeds or beans from plants. Examples of various non-guar galactomannan polymers include Tara gum (3 parts mannose/1 part galactose), Locust bean or Carob (4 parts mannose/1 part galactose), and Cassia gum (5 parts mannose/1 part galactose).

A non-guar galactomannan polymer derivative can have a M. Wt. from about 1,000 g/mol to about 10,000,000 g/mol, and a M.Wt. from about 5,000 g/mol to about 3,000,000 g/mol.

The shampoo compositions described herein can include galactomannan polymer derivatives which have a cationic charge density from about 0.5 meq/g to about 7 meq/g. The galactomannan polymer derivatives can have a cationic charge density from about 1 meq/g to about 5 meq/g. The degree of substitution of the cationic groups onto the galactomannan structure can be sufficient to provide the requisite cationic charge density.

A galactomannan polymer derivative can be a cationic derivative of the non-guar galactomannan polymer, which is obtained by reaction between the hydroxyl groups of the polygalactomannan polymer and reactive quaternary ammonium compounds. Suitable quaternary ammonium compounds for use in forming the cationic galactomannan polymer derivatives include those conforming to the general Formulas II to VI, as defined above.

Cationic non-guar galactomannan polymer derivatives formed from the reagents described above can be represented by the general Formula VII:

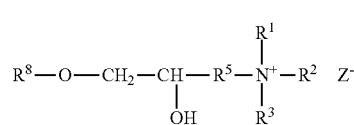

Formula VII wherein R is the gum. The cationic galactomannan derivative can be a gum hydroxypropyltrimethylammonium chloride, which can be more specifically represented by the general Formula VIII:

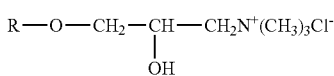

Formula VIII

The galactomannan polymer derivative can be an amphoteric galactomannan polymer derivative having a net positive charge, obtained when the cationic galactomannan polymer derivative further comprises an anionic group.

A cationic non-guar galactomannan can have a ratio of mannose to galactose which is greater than about 4:1, a M.Wt. of about 100,000 g/mol to about 500,000 g/mol, a M.Wt. of about 50,000 g/mol to about 400,000 g/mol, and a cationic charge density from about 1 meq/g to about 5 meq/g, and from about 2 meq/g to about 4 meq/g.

Shampoo compositions can include at least about 0.05% of a galactomannan polymer derivative by weight of the composition. The shampoo compositions can include from about 0.05% to about 2%, by weight of the composition, of a galactomannan polymer derivative.

Cationic Starch Polymers

Suitable cationic polymers can also be water-soluble cationically modified starch polymers. As used herein, the term "cationically modified starch" refers to a starch to which a cationic group is added prior to degradation of the starch to a smaller molecular weight, or wherein a cationic group is added after modification of the starch to achieve a desired molecular weight. The definition of the term "cationically modified starch" also includes amphoterically modified starch. The term "amphoterically modified starch" refers to a starch hydrolysate to which a cationic group and an anionic group are added.

The shampoo compositions described herein can include cationically modified starch polymers at a range of about 0.01% to about 10%, and/or from about 0.05% to about 5%, by weight of the composition.

The cationically modified starch polymers disclosed herein have a percent of bound nitrogen of from about 0.5% to about 4%.

The cationically modified starch polymers can have a molecular weight from about 850,000 g/mol to about 15,000,000 g/mol and from about 900,000 g/mol to about 5,000,000 g/mol.

Cationically modified starch polymers can have a charge density of from about 0.2 meq/g to about 5 meq/g, and from about 0.2 meq/g to about 2 meq/g. The chemical modification to obtain such a charge density can include the addition of amino and/or ammonium groups into the starch molecules. Non-limiting examples of such ammonium groups can include substituents such as hydroxypropyl trimmonium chloride, trimethylhydroxypropyl ammonium chloride, dimethylstearylhydroxypropyl ammonium chloride, and dimethyldodecylhydroxypropyl ammonium chloride. Further details are described in Solarek, D. B., Cationic Starches in Modified Starches: Properties and Uses, Wurzburg, O. B., Ed., CRC Press, Inc., Boca Raton, Fla. 1986, pp 113-125 which is hereby incorporated by reference. The cationic groups can be added to the starch prior to degradation to a smaller molecular weight or the cationic groups may be added after such modification.

A cationically modified starch polymer can have a degree of substitution of a cationic group from about 0.2 to about 2.5. As used herein, the "degree of substitution" of the cationically modified starch polymers is an average measure of the number of hydroxyl groups on each anhydroglucose unit which is derivatized by substituent groups. Since each anhydroglucose unit has three potential hydroxyl groups available for substitution, the maximum possible degree of substitution is 3. The degree of substitution is expressed as the number of moles of substituent groups per mole of anhydroglucose unit, on a molar average basis. The degree of substitution can be determined using proton nuclear magnetic resonance spectroscopy ("$^1$H NMR") methods well known in the art. Suitable $^1$H NMR techniques include those described in "Observation on NMR Spectra of Starches in Dimethyl Sulfoxide, Iodine-Complexing, and Solvating in Water-Dimethyl Sulfoxide", Qin-Ji Peng and Arthur S. Perlin, Carbohydrate Research, 160 (1987), 57-72; and "An Approach to the Structural Analysis of Oligosaccharides by NMR Spectroscopy", J. Howard Bradbury and J. Grant Collins, Carbohydrate Research, 71, (1979), 15-25.

The source of starch before chemical modification can be selected from a variety of sources such as tubers, legumes, cereal, and grains. For example, starch sources can include corn starch, wheat starch, rice starch, waxy corn starch, oat starch, cassaya starch, waxy barley, waxy rice starch, glutenous rice starch, sweet rice starch, amioca, potato starch, tapioca starch, oat starch, sago starch, sweet rice, or mixtures thereof. Suitable cationically modified starch polymers can be selected from degraded cationic maize starch, cationic tapioca, cationic potato starch, and mixtures thereof. Cationically modified starch polymers are cationic corn starch and cationic tapioca.

The starch, prior to degradation or after modification to a smaller molecular weight, can include one or more additional modifications. For example, these modifications may include cross-linking, stabilization reactions, phosphorylations, and hydrolyzations. Stabilization reactions can include alkylation and esterification.

Cationically modified starch polymers can be included in a shampoo composition in the form of hydrolyzed starch (e.g., acid, enzyme, or alkaline degradation), oxidized starch (e.g., peroxide, peracid, hypochlorite, alkaline, or any other oxidizing agent), physically/mechanically degraded starch (e.g., via the thermo-mechanical energy input of the processing equipment), or combinations thereof.

The starch can be readily soluble in water and can form a substantially translucent solution in water. The transparency of the composition is measured by Ultra-Violet/Visible ("UV/VIS") spectrophotometry, which determines the absorption or transmission of UV/VIS light by a sample, using a Gretag Macbeth Colorimeter Color. A light wavelength of 600 nm has been shown to be adequate for characterizing the degree of clarity of shampoo compositions.

Cationic Copolymer of an Acrylamide Monomer and a Cationic Monomer

A shampoo composition can include a cationic copolymer of an acrylamide monomer and a cationic monomer, wherein the copolymer has a charge density of from about 1.0 meq/g to about 3.0 meq/g. The cationic copolymer can be a synthetic cationic copolymer of acrylamide monomers and cationic monomers.

Suitable cationic polymers can include:
(i) an acrylamide monomer of the following Formula IX:

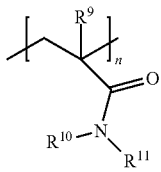

Formula IX where $R^9$ is H or $C_{1-4}$ alkyl; and $R^{10}$ and $R^{11}$ are independently selected from the group consisting of H, $C_{1-4}$ alkyl, $CH_2OCH_3$, $CH_2OCH_2CH(CH_3)_2$, and phenyl, or together are $C_{3-6}$ cycloalkyl; and (ii) a cationic monomer conforming to Formula X:

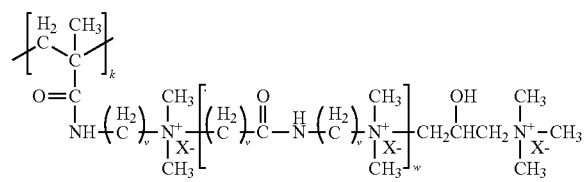

Formula X where k=1, each of v, v', and v" is independently an integer of from 1 to 6, w is zero or an integer of from 1 to 10, and $X^-$ is an anion.

A cationic monomer can conform to Formula X where k=1, v=3 and w=0, z=1 and $X^-$ is $Cl^-$ to form the following structure (Formula XI):

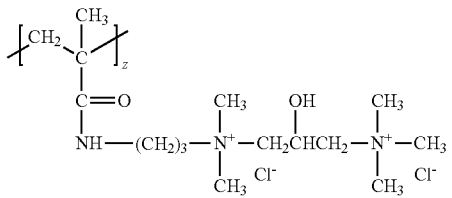

Formula XI

As can be appreciated, the above structure can be referred to as diquat.

A cationic monomer can conform to Formula X wherein v and v" are each 3, v'=1, w=1, y=1 and $X^-$ is $Cl^-$, to form the following structure of Formula XII:

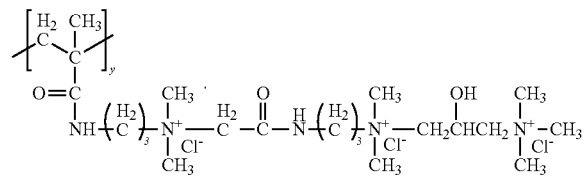

Formula XII

The structure of Formula XII can be referred to as triquat.
The acrylamide monomer can be either acrylamide or methacrylamide.

The cationic copolymer can be AM:TRIQUAT which is a copolymer of acrylamide and 1,3-Propanediaminium,N-[2-[[[dimethyl[3-[(2-methyl-1-oxo-2-propenyl)amino]propyl]ammonio]acetyl]amino]ethyl]2-hydroxy-N,N,N',N',N'-pentamethyl-, trichloride. AM:TRIQUAT is also known as polyquaternium 76 (PQ76). AM:TRIQUAT can have a charge density of 1.6 meq/g and a M.Wt. of 1.1 million g/mol.

The cationic copolymer can include an acrylamide monomer and a cationic monomer, wherein the cationic monomer is selected from the group consisting of: dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide; ethylenimine, vinylamine, 2-vinylpyridine, 4- vinylpyridine; trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, and mixtures thereof.

The cationic copolymer can include a cationic monomer selected from the group consisting of: trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, and mixtures thereof.

The cationic copolymer can be formed from (1) copolymers of (meth)acrylamide and cationic monomers based on (meth)acrylamide, and/or hydrolysis-stable cationic monomers, (2) terpolymers of (meth)acrylamide, monomers based on cationic (meth)acrylic acid esters, and monomers based on (meth)acrylamide, and/or hydrolysis-stable cationic monomers. Monomers based on cationic (meth)acrylic acid esters can be cationized esters of the (meth)acrylic acid containing a quaternized N atom. Cationized esters of the (meth)acrylic acid containing a quaternized N atom can be quaternized dialkylaminoalkyl (meth)acrylates with $C_1$ to $C_3$ in the alkyl and alkylene groups. The cationized esters of the (meth)acrylic acid containing a quaternized N atom can be selected from the group consisting of: ammonium salts of dimethylaminomethyl (meth)acrylate, dimethylaminoethyl (meth)acrylate, dimethylaminopropyl (meth)acrylate, diethylaminomethyl (meth)acrylate, diethylaminoethyl (meth)acrylate; and diethylaminopropyl (meth)acrylate quaternized with methyl chloride. The cationized esters of the (meth)acrylic acid containing a quaternized N atom can be dimethylaminoethyl acrylate, which is quaternized with an alkyl halide, or with methyl chloride or benzyl chloride or dimethyl sulfate (ADAME-Quat). The cationic monomer when based on (meth)acrylamides are quaternized dialkylaminoalkyl(meth)acrylamides with $C_1$ to $C_3$ in the alkyl and alkylene groups, or dimethylaminopropylacrylamide, which is quaternized with an alkyl halide, or methyl chloride or benzyl chloride or dimethyl sulfate.

The cationic monomer based on a (meth)acrylamide can be a quaternized dialkylaminoalkyl(meth)acrylamide with $C_1$ to $C_3$ in the alkyl and alkylene groups. The cationic monomer based on a (meth)acrylamide can be dimethylaminopropylacrylamide, which is quaternized with an alkyl halide, especially methyl chloride or benzyl chloride or dimethyl sulfate.

The cationic monomer can be a hydrolysis-stable cationic monomer. Hydrolysis-stable cationic monomers can be, in addition to a dialkylaminoalkyl(meth)acrylamide, any monomer that can be regarded as stable to the OECD hydrolysis test. The cationic monomer can be hydrolysis-stable and the hydrolysis-stable cationic monomer can be selected from the group consisting of: diallyldimethylammonium chloride and water-soluble, cationic styrene derivatives.

The cationic copolymer can be a terpolymer of acrylamide, 2-dimethylammoniumethyl (meth)acrylate quaternized with methyl chloride (ADAME-Q) and 3-dimethylammoniumpropyl(meth)acrylamide quaternized with methyl chloride (DIMAPA-Q). The cationic copolymer can be formed from acrylamide and acrylamidopropyltrimethylammonium chloride, wherein the acrylamidopropyltrimethylammonium chloride has a charge density of from about 1.0 meq/g to about 3.0 meq/g.

The cationic copolymer can have a charge density of from about 1.1 meq/g to about 2.5 meq/g, from about 1.1 meq/g to about 2.3 meq/g, from about 1.2 meq/g to about 2.2 meq/g, from about 1.2 meq/g to about 2.1 meq/g, from about 1.3 meq/g to about 2.0 meq/g, and from about 1.3 meq/g to about 1.9 meq/g.

The cationic copolymer can have a M.Wt. from about 100 thousand g/mol to about 2 million g/mol, from about 300 thousand g/mol to about 1.8 million g/mol, from about 500 thousand g/mol to about 1.6 million g/mol, from about 700 thousand g/mol to about 1.4 million g/mol, and from about 900 thousand g/mol to about 1.2 million g/mol.

The cationic copolymer can be a trimethylammoniopropylmethacrylamide chloride-N-Acrylamide copolymer, which is also known as AM:MAPTAC. AM:MAPTAC can have a charge density of about 1.3 meq/g and a M.Wt. of about 1.1 million g/mol. The cationic copolymer can be AM:ATPAC. AM:ATPAC can have a charge density of about 1.8 meq/g and a M.Wt. of about 1.1 million g/mol.

Synthetic Polymers

A cationic polymer can be a synthetic polymer that is formed from:
i) one or more cationic monomer units, and optionally
ii) one or more monomer units bearing a negative charge, and/or
iii) a nonionic monomer, wherein the subsequent charge of the copolymer is positive. The ratio of the three types of monomers is given by "m", "p" and "q" where "m" is the number of cationic monomers, "p" is the number of monomers bearing a negative charge and "q" is the number of nonionic monomers The cationic polymers can be water soluble or dispersible, non-crosslinked, and synthetic cationic polymers which have the structure of Formula XIII:

Formula XIII

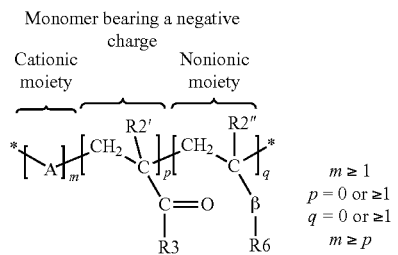

$m \geq 1$
$p = 0$ or $\geq 1$
$q = 0$ or $\geq 1$
$m \geq p$ where A, may be one or more of the following cationic moieties:

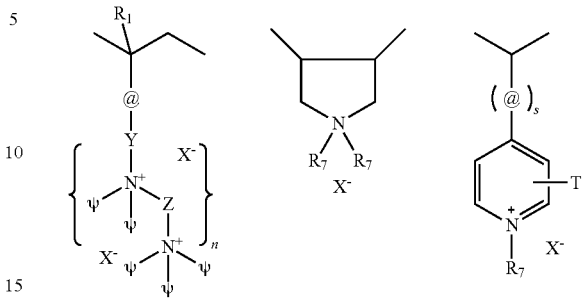

where @=amido, alkylamido, ester, ether, alkyl or alkylaryl;
where Y=C1-C22 alkyl, alkoxy, alkylidene, alkyl or aryloxy;
where ψ=C1-C22 alkyl, alkyloxy, alkyl aryl or alkyl arylox;.
where Z=C1-C22 alkyl, alkyloxy, aryl or aryloxy;
where R1=H, C1-C4 linear or branched alkyl;
where s=0 or 1, n=0 or 1;
where T and R7=C1-C22 alkyl; and
where X-=halogen, hydroxide, alkoxide, sulfate or alkylsulfate.

Where the monomer bearing a negative charge is defined by R2'=H, $C_1$-$C_4$ linear or branched alkyl and R3 is:

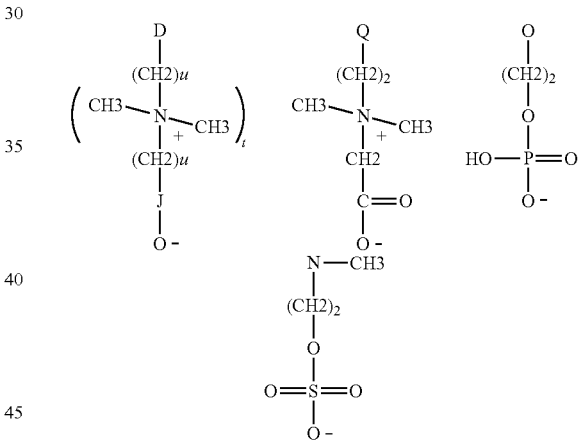

where D=O, N, or S;
where Q=$NH_2$ or O;
where u=1-6;
where t=0-1; and
where J=oxygenated functional group containing the following elements P, S, C.

Where the nonionic monomer is defined by R2"=H, $C_1$-$C_4$ linear or branched alkyl, R6=linear or branched alkyl, alkyl aryl, aryl oxy, alkyloxy, alkylaryl oxy and β is defined as

and where G' and G" are, independently of one another, O, S or N—H and L=0 or 1.

Suitable monomers can include aminoalkyl (meth)acrylates, (meth)aminoalkyl (meth)acrylamides; monomers comprising at least one secondary, tertiary or quaternary amine function, or a heterocyclic group containing a nitrogen atom, vinylamine or ethylenimine; diallyldialkyl ammonium salts; their mixtures, their salts, and macromonomers deriving from therefrom.

Further examples of suitable cationic monomers can include dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide, ethylenimine, vinylamine, 2-vinylpyridine, 4-vinylpyridine, trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride.

Suitable cationic monomers can include quaternary monomers of formula —$NR_3^+$, wherein each R can be identical or different, and can be a hydrogen atom, an alkyl group comprising 1 to 10 carbon atoms, or a benzyl group, optionally carrying a hydroxyl group, and including an anion (counter-ion). Examples of suitable anions include halides such as chlorides, bromides, sulphates, hydrosulphates, alkylsulphates (for example comprising 1 to 6 carbon atoms), phosphates, citrates, formates, and acetates.

Suitable cationic monomers can also include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride. Additional suitable cationic monomers can include trimethyl ammonium propyl (meth)acrylamido chloride.

Examples of monomers bearing a negative charge include alpha ethylenically unsaturated monomers including a phosphate or phosphonate group, alpha ethylenically unsaturated monocarboxylic acids, monoalkylesters of alpha ethylenically unsaturated dicarboxylic acids, monoalkylamides of alpha ethylenically unsaturated dicarboxylic acids, alpha ethylenically unsaturated compounds comprising a sulphonic acid group, and salts of alpha ethylenically unsaturated compounds comprising a sulphonic acid group.

Suitable monomers with a negative charge can include acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropanesulphonic acid (AMPS), salts of acrylamido-2-methylpropanesulphonic acid, and styrenesulphonate (SS).

Examples of nonionic monomers can include vinyl acetate, amides of alpha ethylenically unsaturated carboxylic acids, esters of an alpha ethylenically unsaturated monocarboxylic acids with an hydrogenated or fluorinated alcohol, polyethylene oxide (meth)acrylate (i.e. polyethoxylated (meth)acrylic acid), monoalkylesters of alpha ethylenically unsaturated dicarboxylic acids, monoalkylamides of alpha ethylenically unsaturated dicarboxylic acids, vinyl nitriles, vinylamine amides, vinyl alcohol, vinyl pyrolidone, and vinyl aromatic compounds.

Suitable nonionic monomers can also include styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, 2-ethyl-hexyl methacrylate, 2-hydroxyethylacrylate and 2-hydroxyethylmethacrylate.

The anionic counterion ($X^-$) in association with the synthetic cationic polymers can be any known counterion so long as the polymers remain soluble or dispersible in water, in the shampoo composition, or in a coacervate phase of the shampoo composition, and so long as the counterions are physically and chemically compatible with the essential components of the shampoo composition or do not otherwise unduly impair product performance, stability or aesthetics. Non limiting examples of suitable counterions can include halides (e.g., chlorine, fluorine, bromine, iodine), sulfate, and methylsulfate.

The cationic polymer described herein can also aid in repairing damaged hair, particularly chemically treated hair by providing a surrogate hydrophobic F-layer. The microscopically thin F-layer provides natural weatherproofing, while helping to seal in moisture and prevent further damage. Chemical treatments damage the hair cuticle and strip away its protective F-layer. As the F-layer is stripped away, the hair becomes increasingly hydrophilic. It has been found that when lyotropic liquid crystals are applied to chemically treated hair, the hair becomes more hydrophobic and more virgin-like, in both look and feel. Without being limited to any theory, it is believed that the lyotropic liquid crystal complex creates a hydrophobic layer or film, which coats the hair fibers and protects the hair, much like the natural F-layer protects the hair. The hydrophobic layer can return the hair to a generally virgin-like, healthier state. Lyotropic liquid crystals are formed by combining the synthetic cationic polymers described herein with the aforementioned anionic detersive surfactant component of the shampoo composition. The synthetic cationic polymer has a relatively high charge density. It should be noted that some synthetic polymers having a relatively high cationic charge density do not form lyotropic liquid crystals, primarily due to their abnormal linear charge densities. Such synthetic cationic polymers are described in PCT Patent App. No. WO 94/06403 which is incorporated by reference. The synthetic polymers described herein can be formulated in a stable shampoo composition that provides improved conditioning performance, with respect to damaged hair.

Cationic synthetic polymers that can form lyotropic liquid crystals have a cationic charge density of from about 2 meq/gm to about 7 meq/gm, and/or from about 3 meq/gm to about 7 meq/gm, and/or from about 4 meq/gm to about 7 meq/gm. The cationic charge density is about 6.2 meq/gm. The polymers also have a M. Wt. of from about 1,000 to about 5,000,000, and/or from about 10,000 to about 2,000,000, and/or from about 100,000 to about 2,000,000.

Cationic synthetic polymers that provide enhanced conditioning and deposition of benefit agents but do not necessarily form lytropic liquid crystals can have a cationic charge density of from about 0.7 meq/gm to about 7 meq/gm, and/or from about 0.8 meq/gm to about 5 meq/gm, and/or from about 1.0 meq/gm to about 3 meq/gm. The polymers also have a M.Wt. of from about 1,000 g/mol to about 5,000,000 g/mol, from about 10,000 g/mol to about 2,000,000 g/mol, and from about 100,000 g/mol to about 2,000,000 g/mol.

Cationic Cellulose Polymer

Suitable cationic polymers can be cellulose polymers. Suitable cellulose polymers can include salts of hydroxyethyl cellulose reacted with trimethyl ammonium substituted epoxide, referred to in the industry (CTFA) as Polyquaternium 10 and available from Dwo/ Amerchol Corp. (Edison, N.J., USA) in their Polymer LR, JR, and KG series of polymers. Other suitable types of cationic cellulose can include the polymeric quaternary ammonium salts of hydroxyethyl cellulose reacted with lauryl dimethyl ammonium-substituted epoxide referred to in the industry (CTFA) as Polyquaternium 24. These materials are available from Dow/Amerchol Corp. under the tradename Polymer LM-200. Other suitable types of cationic cellulose can include the polymeric quaternary ammonium salts of hydroxyethyl cellulose reacted with lauryl dimethyl ammonium-substituted epoxide and trimethyl ammonium substituted epoxide referred to in the industry (CTFA) as Polyquaternium 67. These materials are available from Dow/Amerchol Corp. under the tradename SoftCAT Polymer SL-5, SoftCAT Polymer SL-30, Polymer SL-60, Polymer SL-100, Polymer SK-L, Polymer SK-M, Polymer SK-MH, and Polymer SK-H.

Additional cationic polymers are also described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)), which is incorporated herein by reference.

Techniques for analysis of formation of complex coacervates are known in the art. For example, microscopic analyses of the compositions, at any chosen stage of dilution, can be utilized to identify whether a coacervate phase has formed. Such coacervate phase can be identifiable as an additional emulsified phase in the composition. The use of dyes can aid in distinguishing the coacervate phase from other insoluble phases dispersed in the composition. Additional details about the use of cationic polymers and coacervates are disclosed in U.S. Pat. No. 9,272,164 which is incorporated by reference.

Silicone

The shampoo composition can include a silicone conditioning agent. The silicone conditioning agent can be in the benefit phase and/or the cleansing phase. Suitable silicone conditioning agents can include volatile silicone, non-volatile silicone, or combinations thereof. If including a silicone conditioning agent, the agent can be included from about 0.01% to about 10%, by weight of the composition, from about 0.1% to about 8%, from about 0.1% to about 5%, and/or from about 0.2% to about 2%, by weight of the cleansing phase, benefit phase, or composition. Examples of suitable silicone conditioning agents, and optional suspending agents for the silicone, are described in U.S. Reissue Pat. No. 34,584, U.S. Pat. Nos. 5,104,646, and 5,106,609, each of which is incorporated by reference herein. Suitable silicone conditioning agents can have a viscosity, as measured at 25° C., from about 20 centistokes ("csk") to about 2,000,000 csk, from about 1,000 csk to about 1,800,000 csk, from about 50,000 csk to about 1,500,000 csk, and from about 100,000 csk to about 1,500,000 csk.

The dispersed silicone conditioning agent particles can have a volume average particle diameter ranging from about 0.01 micrometer to about 50 micrometer. For small particle application to hair, the volume average particle diameters can range from about 0.01 micrometer to about 4 micrometer, from about 0.01 micrometer to about 2 micrometer, from about 0.01 micrometer to about 0.5 micrometer. For larger particle application to hair, the volume average particle diameters typically range from about 5 micrometer to about 125 micrometer, from about 10 micrometer to about 90 micrometer, from about 15 micrometer to about 70 micrometer, and/or from about 20 micrometer to about 50 micrometer.

Additional material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989), which is incorporated herein by reference.

Silicone emulsions suitable for the shampoo compositions described herein can include emulsions of insoluble polysiloxanes prepared in accordance with the descriptions provided in U.S. Pat. No. 4,476,282 and U.S. Patent Application Publication No. 2007/0276087 each of which is incorporated herein by reference. Suitable insoluble polysiloxanes include polysiloxanes such as alpha, omega hydroxy-terminated polysiloxanes or alpha, omega alkoxy-terminated polysiloxanes having a molecular weight within the range from about 50,000 to about 500,000 g/mol. The insoluble polysiloxane can have an average molecular weight within the range from about 50,000 to about 500,000 g/mol. For example, the insoluble polysiloxane may have an average molecular weight within the range from about 60,000 to about 400,000; from about 75,000 to about 300,000; from about 100,000 to about 200,000; or the average molecular weight may be about 150,000 g/mol. The insoluble polysiloxane can have an average particle size within the range from about 30 nm to about 10 micron. The average particle size may be within the range from about 40 nm to about 5 micron, from about 50 nm to about 1micron, from about 75 nm to about 500 nm, or about 100 nm, for example.

Other classes of silicones suitable for the shampoo compositions described herein can include i) silicone fluids, including silicone oils, which are flowable materials having viscosity less than about 1,000,000 csk as measured at 25° C.; ii) aminosilicones, which contain at least one primary, secondary or tertiary amine; iii) cationic silicones, which contain at least one quaternary ammonium functional group; iv) silicone gums; which include materials having viscosity greater or equal to 1,000,000 csk as measured at 25° C.; v) silicone resins, which include highly cross-linked polymeric siloxane systems; vi) high refractive index silicones, having refractive index of at least 1.46, and vii) mixtures thereof.

Alternatively, the shampoo composition can be substantially free of silicones.

Aqueous Carrier

The cleansing phase and the benefit phase can both include an aqueous carrier. Accordingly, the formulations of the shampoo composition can be in the form of a pourable liquid (under ambient conditions). The cleansing phase can contain an aqueous carrier that can be present from about 15% to about 95%, alternatively from about 50% to about 93%, alternatively from about 60% to about 92%, alternatively from about 70% to about 90%, alternatively from about 72% to about 88%, and alternatively from about 75% to about 85%, by weight of the cleansing phase. The benefit phase can contain an aqueous carrier that can be present from about 25% to about 98%, alternatively from about 40% to about 95%, alternatively from about 50% to about 90%, alternatively from about 60% to about 85%, alternatively from about 65% to about 83%, by weight of the benefit phase.

The aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The aqueous carriers useful in the shampoo composition can include water. In another example, the shampoo compositions can include water solutions of lower alkyl alcohols and polyhydric alcohols. The lower alkyl alcohols can include monohydric alcohols having 1 to 6 carbons, in one aspect, ethanol and isopropanol. The polyhydric alcohols can include propylene glycol, dipropylene glycol, hexylene glycol, glycerin, and propane diol.

Optional Components

As can be appreciated, shampoo compositions described herein can include a variety of optional components to tailor the properties and characteristics of the composition. As can be appreciated, suitable optional components are well known and can generally include any components which are physically and chemically compatible with the essential components of the shampoo compositions described herein. Optional components should not otherwise unduly impair product stability, aesthetics, or performance. Optional components can be in the cleansing phase and/or the benefit phase. Individual concentrations of optional components can generally range from about 0.001% to about 10%, by weight of a shampoo composition. Optional components in the cleansing phase can be further limited to components which will not impair the clarity of a translucent shampoo composition.

Suitable optional components which can be included in a shampoo composition can include deposition aids, conditioning agents (including hydrocarbon oils, fatty esters, silicones), anti-dandruff agents, viscosity modifiers, dyes, nonvolatile solvents or diluents (water soluble and insoluble), pearlescent aids, foam boosters, pediculocides, pH adjusting agents, perfumes, preservatives, chelants, proteins, skin active agents, sunscreens, UV absorbers, and vitamins. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of non-limiting materials that can be added to the composition herein.

Suitable optional components which can be included in a shampoo composition can include amino acids can be included. Suitable amino acids can include water soluble vitamins such as vitamins B1, B2, B6, B12, C, pantothenic acid, pantothenyl ethyl ether, panthenol, biotin, and their derivatives, water soluble amino acids such as asparagine, alanin, indole, glutamic acid and their salts, water insoluble vitamins such as vitamin A, D, E, and their derivatives, water insoluble amino acids such as tyrosine, tryptamine, and their salts.

Organic Conditioning Materials

The organic conditioning agent of the shampoo compositions described herein can also include at least one organic conditioning material such as oil or wax, either alone or in combination with other conditioning agents, such as the silicones described above. The organic conditioning material can be in the cleansing phase and/or the benefit phase. The organic conditioning agent can be in the benefit phase and/or the cleansing phase. The organic material can be non-polymeric, oligomeric or polymeric. The organic material can be in the form of an oil or wax and can be added in the shampoo formulation neat or in a pre-emulsified form. Suitable examples of organic conditioning materials can include: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M and mixtures thereof.

Emulsifiers

A variety of anionic and nonionic emulsifiers can be used in the shampoo composition including the benefit phase and/or the cleansing phase. The anionic and nonionic emulsifiers can be either monomeric or polymeric in nature. Monomeric examples include, by way of illustrating and not limitation, alkyl ethoxylates, alkyl sulfates, soaps, and fatty esters and their derivatives. Polymeric examples include, by way of illustrating and not limitation, polyacrylates, polyethylene glycols, and block copolymers and their derivatives. Naturally occurring emulsifiers such as lanolins, lecithin and lignin and their derivatives are also non-limiting examples of useful emulsifiers.

Chelating Agents

A chelant can be used in the shampoo composition including the benefit phase and/or the cleansing phase. Suitable chelants include those listed in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996) both incorporated herein by reference. When related to chelants, the term "salts and derivatives thereof" means the salts and derivatives comprising the same functional structure (e.g., same chemical backbone) as the chelant they are referring to and that have similar or better chelating properties. This term include alkali metal, alkaline earth, ammonium, substituted ammonium (i.e. monoethanolammonium, diethanolammonium, triethanolammonium) salts, esters of chelants having an acidic moiety and mixtures thereof, in particular all sodium, potassium or ammonium salts. The term "derivatives" also includes "chelating surfactant" compounds, such as those exemplified in U.S. Pat. No. 5,284,972, and large molecules comprising one or more chelating groups having the same functional structure as the parent chelants, such as polymeric EDDS (ethylenediaminedisuccinic acid) disclosed in U.S. Pat. No. 5,747,440. U.S. Pat. Nos. 5,284,972 and 5,747,440 are each incorporated by reference herein. Suitable chelants can further include histidine.

Levels of an EDDS chelant or histidine chelant in the shampoo compositions can be low. For example, an EDDS chelant or histidine chelant can be included at about 0.01%, by weight. Above about 10% by weight, formulation and/or human safety concerns can arise. The level of an EDDS chelant or histidine chelant can be at least about 0.01%, by weight, at least about 0.05%, by weight, at least about 0.1%, by weight, at least about 0.25%, by weight, at least about 0.5%, by weight, at least about 1%, by weight, or at least about 2%, by weight, by weight of the shampoo composition.

Additional Cosmetic Materials

A shampoo composition can further include one or more additional cosmetic materials. Exemplary additional cosmetic materials can include, but are not limited to, particles, colorants, perfume microcapsules, gel networks, and other insoluble skin or hair conditioning agents such as skin silicones, natural oils such as sunflower oil or castor oil. The additional cosmetic material can be selected from the group consisting of: particles; colorants; perfume microcapsules; gel networks; other insoluble skin or hair conditioning agents such as skin silicones, natural oils such as sun flower oil or castor oil; and mixtures thereof.

Anti-Dandruff Actives

The shampoo compositions may also contain an anti-dandruff active. The anti-dandruff active can be present in the cleansing phase and/or the benefit phase. Soluble anti-dandruff actives, such as piroctone olamine can be present in the cleansing phase or the benefit phase. Non-soluble anti-dandruff actives such as pyridinethione (e.g. zinc pyrithione) can be present in the benefit phase. In some examples, the cleansing phase can be substantially free of non-soluble anti-dandruff actives. Suitable non-limiting examples of anti-dandruff actives include pyridinethione salts, azoles, selenium sulfide, particulate sulfur, keratolytic agents, and mixtures thereof. Such anti-dandruff actives should be physically and chemically compatible with the components of the composition, and should not otherwise unduly impair product stability, aesthetics or performance When present in the composition, the anti-dandruff active is included in an amount from about 0.01% to about 5%, alternatively from about 0.1% to about 3%, and alternatively from about 0.3% to about 2%, by weight of the composition, benefit phase, or cleansing phase.

Test Methods

Hair Wet Feel Friction Measurement (Final Rinse Friction and Initial Rinse Friction)

A switch of 4 grams general population hair at 8 inches length is used for the measurement. Water temperature is set at 100° F., hardness is 7 grain per gallon, and flow rate is 1.6 liter per minute. For shampoos in liquid form, 0.2 ml of a liquid shampoo is applied on the hair switch in a zigzag pattern uniformly to cover the entire hair length, using a syringe. For shampoo in aerosol foam form, foam shampoo is dispensed to a weighing pan on a balance. 0.2 grams of foam shampoo is taken out from weighing pan and applied on the hair switch uniformly to cover the entire hair length via a spatula. The hair switch is then 1st lathered for 30 seconds, rinse with water for 30 seconds, and 2nd lathered for 30 seconds. Water flow rate is then reduced to 0.2 liter per minute. The hair switch is sandwiched with a clamp under 1800 gram of force and pulled through the entire length while the water is running at the low flow rate. The pull time is 30 second. Friction is measured with a friction analyzer with a load cell of 5 kg. Repeat the pull under rinse for total of 21 times. Total 21 friction values are collected. The final rinse friction is the average friction of the last 7 points and initial rinse friction is the average of the initial 7 points. The delta final to initial is calculated by subtracting the final rinse friction from the initial rinse friction.

Light Transmittance

% T can be measured using Ultra-Violet/Visible (UV/VI) spectrophotometry which determines the transmission of UV/VIS light through a sample. A light wavelength of 600 nm has been shown to be adequate for characterizing the degree of light transmittance through a sample. Typically, it is best to follow the specific instructions relating to the specific spectrophotometer being used. In general, the procedure for measuring percent transmittance starts by setting the spectrophotometer to 600 nm. Then a calibration "blank" is run to calibrate the readout to 100 percent transmittance. A single test sample is then placed in a cuvette designed to fit the specific spectrophotometer and care is taken to insure no air bubbles are within the sample before the % T is measured by the spectrophotometer at 600 nm.

EXAMPLES

The shampoo compositions illustrated in the following Examples illustrate specific embodiments of the shampoo compositions of the present invention but are not intended to be limiting thereof. It will be appreciated that other modifications of the present invention within the skill of those in the shampoo formulation art can be undertaken without departing from the spirit and scope of this invention. All exemplified amounts are listed as weight percent's and exclude minor materials such as diluents, preservatives, color solutions, imagery ingredients, botanicals, and so forth, unless otherwise specified. All percentages are based on weight unless otherwise specified.

The exemplified embodiments can provide cleansing of hair or skin, enhanced hair strength benefits (measured as fatty amphiphile penetration into the hair fiber) and improved conditioning and volumizing benefits to the hair. Additionally, in one embodiment of the present invention, where the cleansing phase is visibly clear and the benefit phase is opaque, these visual cues are intuitive to the consumer in better connoting the cleaning and conditioning benefits associated with the respective product phases within the multiphase shampoo.

The shampoo compositions illustrated in the following Examples are prepared by conventional formulation and mixing methods. The gel network benefit phase was prepared as follows. The water is heated to about 74° C. and the fatty compound and secondary surfactant (e.g. Sodium Laureth Sulfate) are added to it. After incorporation, this mixture is passed through a mill and then cooled (e.g. via heat exchanger) to about 32° C. As a result of this cooling step, the fatty alcohol, the secondary surfactant, and the water form a crystalline gel network.

The multiphase shampoo composition can be made by using a piston filler that can accommodate two or more individual product streams during filling. The individual streams can form the aesthetic design in the final shampoo compositions. During filling, special care was taken to minimize air entrapment into the cleansing phase during filling into bottles or other suitable primary packaging. In some examples, bottles can be overfilled using the cleansing phase only, ensuring that any remaining headspace would be displaced/purged from the bottle during pump insertion. In some instances, the bottle was capped with a pump that was carefully placed to minimize displacement of the aesthetic design during filling.

Examples 1-6 in Table 1 (below) are gel networks that could be made and incorporated as the benefit phase in a multiphase shampoo composition. Examples 7 and 8 were made and swirled into a cleansing phase to form a multiphase shampoo composition as described in Table 4, described hereafter.

TABLE 1

Benefit Phase Premix

| | Ex. 1 | Ex. 2 | Ex. 3 | Ex. 4 | Ex. 5 | Ex. 6 | Ex. 7 | Ex. 8 |
|---|---|---|---|---|---|---|---|---|
| Stearyl Alcohol | 8 | 7 | 4 | 5 | 8 | 7 | 8 | 8 |
| Cetyl Alcohol | 4 | 5 | 7 | 5 | 4 | 7 | 4 | 4 |
| Stearic Acid | | | 11 | | | | | |
| Sodium Laureth Sulfate [1] | 11 | | | | | | 11 | 11 |
| Sodium Lauryl Sulfate | | | | | | 11 | | |
| Sodium Cocoyl Isethionate | | | | | 4 | | | |
| Sodium Methyl Cocoyl Taurate | | 10 | | | | | | |
| Cocamidopropyl Betaine | 1 | | | | 7 | | 1 | 1 |
| Behenyltrimethylammonium Chloride | | | | 10 | | | | |
| Guar Hydroxypropyltrimonium Chloride [2] | | 0.5 | | | | | | |
| Guar Hydroxypropyltrimonium Chloride [3] | | | | | | 1 | | |
| Polyquaternium-10 [4] | | 0.5 | | | | | | |
| Polyquaternium-6 [5] | | | | | | | 1 | 1 |
| Dimethicone [6] | | | | 1 | | | | |
| Dimethicone [7] | | | | | | 5 | | |
| Dimethicone [8] | | | | 1 | | | | |
| Glycerin | | | | 1 | | | | |
| Dye/Pigment | | | | | | | 1 | 0.2 |
| Fragrance | | | | | | 0.5 | | |
| 5-Chloro-2-methyl-4-isothiazolin-3-one [9] | 0.0005 | 0.0005 | 0.0005 | 0.0005 | 0.0005 | | 0.0005 | 0.0005 |
| Sodium Benzoate | | | | | | 0.25 | | |
| Citric Acid/Sodium Citrate Dihydrate/HCl/NaOH | | | | Adjust to pH ~5-7 | | | | |
| Water | QS | QS | QS | QS | QS | QS | QS | QS |

[1] Sodium Laureth-n Sulfate, where n ≥ 1 and ≤ 3
[2] N-Hance ™ BF17 (Ashland ™)
[3] N-Hance ™ 3196 (Ashland ™)
[4] Polymer KG30 M (Dow ® Chemical Company) with a charge density of 1.97 meq/gm and molecular weight of 2,000,000
[5] Mirapol ® 100S (Solvay ®)
[6] CF330 m (Momentive ™ Performance Materials)
[7] Belsil ® DM 5500 E (WACKER)
[8] Dow Corning ® 1872 (Dow Corning ® Corporation)
[9] Kathon ™ CG (DuPont ®)

Examples A-F, H, and J-L in Table 2 and Table 3 (below) are cleansing shampoos that could be used as the cleansing phase in a multiphase shampoo composition. Examples G and I were made and are the cleansing phases of multiphase shampoo compositions as described in Table 4, described hereafter. At minimum, Examples D, E, and F are expected to be clear or almost clear. Examples G and I were clear.

TABLE 2

Cleansing Phase Premix

| Ingredient - Cleansing Phase | Ex. A | Ex. B | Ex. C | Ex. D | Ex. E | Ex. F |
|---|---|---|---|---|---|---|
| Sodium Laureth Sulfate [1] | 10.00 | | 10.00 | | | 14.00 |
| Sodium Lauryl Sulfate | 1.50 | 1.50 | 6.00 | | | |
| Sodium C12-18 Alkyl Sulfate | | 8.50 | | | | |
| Sodium Cocoyl Isethionate | | | | 6.00 | | |
| Sodium Lauryl Sarcosinate | | | | 2.50 | | |
| Disodium Cocoyl Glutamate | | | | | 11.00 | |
| Decyl Glucoside | | | | | 12.00 | |
| Cocamidopropyl Betaine | 2.00 | 2.00 | | 8.50 | | |
| Cocamide MEA | | 1.00 | | | | |
| Ketoconazole | | | 1.00 | | | |
| Climbazole | | 1.50 | | | | |
| Piroctone Olamine [2] | | | | | | 0.50 |
| Cationic Galactomannan [3] | 0.40 | | 0.40 | | | |
| Cationic Galactomannan [4] | | 0.10 | | | | |

TABLE 2-continued

Cleansing Phase Premix

| Ingredient - Cleansing Phase | Ex. A | Ex. B | Ex. C | Ex. D | Ex. E | Ex. F |
|---|---|---|---|---|---|---|
| Guar Hydroxypropyl Trimonium Chloride [5] | | 0.20 | | | 1.00 | |
| Guar Hydroxypropyl Trimonium Chloride [6] | 0.10 | | | | | |
| Polyquaternium-10 [7] | | | | 0.55 | | |
| Polyquaternium-10 [8] | | | 0.50 | | | |
| Polyquaternium-6 [9] | 0.03 | | | | | |
| Dimethicone [10] | | 0.25 | | | | |
| Dimethicone [11] | | | | 1.00 | | |
| Hydrogenated Castor Oil | | 0.03 | | | | |
| Acrylates Copolymer [12] | 1.75 | 1.00 | | 1.50 | 1.50 | |
| Acrylates Crosspolymer [13] | | | 1.50 | | | 3.00 |
| 5-Chloro-2-methyl-4-isothiazolin-3-one [14] | 0.0005 | 0.0005 | 0.0005 | | | 0.0005 |
| Sodium Benzoate | 0.25 | 0.25 | 0.25 | 0.25 | 0.60 | 0.25 |
| Sodium Salicylate | | | | 0.50 | | |
| Tetrasodium EDTA | 0.16 | | | 0.16 | | 0.16 |
| Benzyl Alcohol | | 0.03 | 0.03 | | | |
| Perfume | 0.70 | 0.70 | 0.70 | 0.70 | 0.70 | 1.00 |
| Citric Acid/Sodium Citrate Dihydrate/HCl/NaOH | Adjust to pH ~5-7 | | | | | |
| Sodium Chloride/Ammonium Xylene Sulfonate | Adjust to viscosity of ~6-14 Pa · s | | | | | |
| Water | QS | QS | QS | QS | QS | QS |

TABLE 3

Cleansing Phase Premix

| Ingredient - Cleansing Phase | Ex. G | Ex. H | Ex. I | Ex. J | Ex. K | Ex. L |
|---|---|---|---|---|---|---|
| Sodium Laureth Sulfate [1] | 13.00 | 15.30 | 13.00 | | | |
| Sodium Lauryl Sulfate | | | | 16.00 | 8.00 | |
| Sodium C12-18 Alkyl Sulfate | | | | | 8.00 | |
| Sodium Cocoyl Isethionate | | | | | | 6.00 |
| Sodium Lauryl Sarcosinate | | | | | | 2.00 |
| Disodium Cocoyl Glutamate | | | | | | |
| Decyl Glucoside | | | | | | |
| Cocamidopropyl Betaine | | 2.30 | | | | 12.00 |
| Cocamide MEA | | | | | | |
| Ketoconazole | | | | | | |
| Climbazole | | | | | | |
| Piroctone Olamine [2] | | | | | | |
| Cationic Galactomannan [3] | | | | | | |
| Cationic Galactomannan [4] | | | | | | |
| Guar Hydroxypropyl Trimonium Chloride [5] | | | | | 2.00 | |
| Guar Hydroxypropyl Trimonium Chloride [6] | | | | | | |
| Polyquaternium-10 [7] | 0.20 | | 0.20 | | | |
| Polyquaternium-10 [8] | | | | | | 1.00 |
| Polyquaternium-6 [9] | | | | | | 0.10 |
| Dimethicone [10] | | | | | 2.00 | |
| Dimethicone [11] | | | | 3.00 | | |
| Glycerin | | 0.57 | | | | |
| Hydrogenated Castor Oil | | | | | | |
| Acrylates Copolymer [12] | | 1.70 | | 3.50 | | |
| Acrylates Crosspolymer [13] | 2.60 | | 2.60 | | 6.00 | 4.00 |
| 5-Chloro-2-methyl-4-isothiazolin-3-one [14] | 0.0005 | 0.0006 | 0.0005 | 0.0005 | 0.0005 | 0.0005 |
| Sodium Benzoate | 0.25 | 0.25 | 0.25 | 0.25 | 0.25 | 0.25 |
| Sodium Salicylate | | | | | | |
| Tetrasodium EDTA | 0.16 | 0.18 | 0.16 | 0.16 | 0.16 | 0.16 |
| Benzyl Alcohol | | | | | | |
| Perfume | 1.00 | 0.90 | 1.30 | 0.70 | 0.70 | 1.00 |
| Citric Acid/Sodium Citrate Dihydrate/HCl/NaOH | Adjust to pH ~5-7 | | | | | |
| Sodium Chloride/Ammonium Xylene Sulfonate | Adjust to viscosity of ~4-14 Pa · s | | | | | |
| Water | QS | QS | QS | QS | QS | QS |

(1) Sodium Laureth-n Sulfate, where n≥1 and ≤3
(2) Octopirox® (Clariant®)
(3) Cationic Galactomannan (with Mol. W. of –200,000; Char. Den.=3.0 meq/g)
(4) Cationic Galactomannan (with Mol. W. of –200,000; Char. Den.=0.7 meq/g)
(5) Jaguar® Excel (Solvay®)
(6) N-Hance™ 3196 (Ashland™)
(7) UCARE™ LR-30M (Dow® Chemical Company)
(8) Polymer KG30M (Dow® Chemical Company) with a charge density of 1.97 meq/gm and molecular weight of 2,000,000
(9) Mirapol® 100S (Solvay®)
(10) Belsil® DM 5500 E (WACKER)
(11) Dow Corning® 1872 (Dow Corning® Corporation)
(12) Carbopol® Aqua SF1 (Lubrizol® Advanced Materials)
(13) Carbopol® Aqua SF2 (Lubrizol Advanced Materials)
(14) Kathon™ CG (DuPont®)

The Examples in Table 4, below, are examples of the multiphase shampoo compositions that can be made by combining the cleansing phase in Table 2 with the benefit phase in Table 1. Example 16 was made by swirling Example 7 in Table 1 into Example G in Table 2. A photograph of Example 16 is in FIG. 1. Example 17 was made by swirling Example 8 in Table 1 into Example I in Table 3. A photograph of Example 17 is in FIG. 2.

TABLE 4

Multiphase Shampoo compositions

| | Ex. 9 | Ex. 10 | Ex. 11 | Ex. 12 | Ex. 13 | Ex. 14 | Ex. 15 | Ex. 16 | Ex. 17 |
|---|---|---|---|---|---|---|---|---|---|
| Any one or combination of Benefit Phase Premixes Ex. 1-8 | 1 | 5 | 10 | 20 | 30 | 50 | 80 | | |
| Benefit Phase Premix Ex. 7 | | | | | | | | 5 | |
| Benefit Phase Premix Ex. 8 | | | | | | | | | 20 |
| Any one or combination of Cleansing Phase Premixes Ex. A-L | 99 | 95 | 90 | 80 | 70 | 50 | 20 | | |
| Cleansing Phase Premix Ex. G | | | | | | | | 95 | |
| Cleansing Phase Premix Ex. I | | | | | | | | | 80 |

Combinations

A. A container configured to hold a multiphase shampoo composition comprising:
   a. a cleansing phase comprising a detersive surfactant and an aqueous carrier;
   b. a benefit phase comprising a gel network comprising:
      i. a fatty compound selected from the group consisting of fatty alcohols, fatty acids, and combinations thereof;
      ii. a secondary surfactant selected from the group consisting of anionic, amphoteric, zwitterionic, cationic and combinations thereof;
      wherein the cleansing phase and the benefit phase are visually discrete phases, in physical contact, and form an aesthetic design suspended across at least a portion of the container;
      wherein the cleansing phase and the benefit phase are stable.

B. The container of paragraph A, wherein the cleansing phase comprises from about 3% to about 40%, preferably from about 5% to about 30%, more preferably from about 6% to about 25%, and even more preferably from about 8% to about 25%, by weight of the cleansing phase, detersive surfactant.

C. The container of paragraphs A-B, wherein the cleansing phase is substantially free of sulfate-based surfactants, and wherein the detersive surfactant is selected from the group consisting of isethionates, sarcosinates, sulfonates, sulfosuccinates, sulfoacetates, acyl glycinates, acyl alaninates, acyl glutamates, lactates, lactylates, glucose carboxylates, amphoacetates, taurates, phosphate esters, and mixtures thereof.

D. The container of paragraphs A-B, wherein the anionic surfactant is selected from the group consisting of sodium lauryl sulfate, sodium laureth sulfate, and combinations thereof.

E. The container of paragraphs A-D, wherein the shampoo compositions comprises from from about 1% to about 90%, preferably from about 2% to about 50%, more preferably from about 5% to about 40%, even more preferably from about 7% to about 30%, and even more preferably from about 10% to about 25%, by weight of the shampoo composition, of the benefit phase.

F. The container of paragraphs A-E, wherein the benefit phase comprises from about 2.8% to about 25%, preferably from about 4% to about 23%, more preferably from about 5% to about 20%, and even more preferably from about 6% to about 18%, by weight of the benefit phase, fatty alcohol.

G. The container of paragraphs A-F, wherein the fatty compound of the benefit phase is a fatty alcohol selected from the group consisting of cetyl alcohol, stearyl alcohol, and combinations thereof.

H. The container of paragraphs A-G, wherein the benefit phase comprises from about 0.01% to about 15%, preferably from about 0.5% to about 12%, more preferably from about 0.7% to about 10%, and even more preferably from about 1% to about 6%, by weight of the benefit phase, secondary surfactant.

I. The container of paragraphs A-H, wherein the secondary surfactant is selected from the group consisting of anionic, amphoteric, zwitterionic, and combinations thereof.

J. The container of paragraphs A-H, wherein the benefit phase further comprises a nonionic surfactant.

K. The container of paragraphs A-J, wherein the cleansing phase and the benefit phase further comprise an aqueous carrier.

L. The container of paragraphs A-K, wherein the benefit phase further comprises a material selected from the group consisting of silicone, particulates, mica, and combinations thereof.

M. The container of paragraphs A-L, wherein the benefit phase further comprises from about 0.075% to about 2%, and preferably form about 0.1% to about 1.0%, by weight of the benefit phase, of a cationic deposition polymer.

N. The container of paragraphs A-M, wherein the cationic deposition polymer has a weight average molecular weight of from about 100,000 g/mol to about 3,000,000 g/mol, preferably 300,000 g/mol to about 3,000,000 g/mol.

O. The container of paragraphs A-N, wherein the cationic polymer is selected from the group consisting of cationic guars, cationic cellulose, cationic synthetic homopolymers, cationic synthetic copolymers, cationic synthetic terpolymers, and combinations thereof.

P. The container of paragraphs A-O, wherein the cationic deposition polymer is selected from the group consisting of cationic guars, cationic cellulose, cationic synthetic homopolymers, cationic synthetic copolymers, and combinations thereof.

Q. The container of paragraphs A-P, wherein the cationic polymer is selected from the group consisting of guar hydroxypropyltrimonium chloride, Polyquaternium 10, Polyquaternium 6, and combinations thereof.

R. The container of paragraphs A-Q, wherein the container is a bottle wherein at least a portion of the bottle is transparent and wherein the bottle is substantially free of headspace and substantially free visually discernable air bubbles prior to first use.

S. The container of paragraphs A-R, wherein the cleansing phase comprises a transmittance of at least 70%, preferably at least 80%, and more preferably at least 90%, as determined by the Light Transmittance Method described herein.

T. The container of paragraphs A-S, wherein the benefit phase comprises a transmittance of less than 50%, preferably less than 40%, and most preferably less than 30%, as determined by the Light Transmittance Method described herein.

U. The container of paragraphs A-T, wherein the cleansing phase comprises a yield stress according to the Herschel-Bulkley model @ shear rate $10^{-2}$ to $10^{-4}$ Pa of from about 0.01 to about 20 Pa, preferably from about 0.01 to about 10 Pa, and more preferably from about 0.01 to about 5 dPa.

V. The container of paragraphs A-U, wherein the cleansing phase and/or the benefit phase comprises a viscosity at @ 2 s−1 Pa·s of from about 0.01 to about 15. The cleansing phase can have a viscosity @ 100 s−1 Pa·s of from about 0.1 to about 4 Pa·s, alternatively from about 0.1 to about 2 Pa·s, alternatively from about 0.1 to about 1 Pa·s.

W. The container of paragraphs A-V, wherein the benefit phase comprises a shear stress of about 100 Pa to about 300 Pa at a shear rate of 950 $s^{-1}$, preferably about 130 Pa to about 250 Pa at a shear rate of 950 $s^{-1}$, and more preferably about 160 Pa to about 225 Pa at a shear rate of 950 $s^{-1}$ at 25° C.

X. The container of paragraphs A-W, wherein the cleansing phase further comprises from about 0.05% to about 10%, preferably from about 0.3% to about 5.0%, and more preferably from about 1.5% to about 5.0%, by weight of the cleansing phase, a structurant selected from the group consisting of vinyl polymers, cellulose derivatives and modified cellulose polymers, polyvinylpyrrolidone, polyvinyl alcohol, guar gum, hydroxypropyl guar gum, xanthan gum, arabia gum, tragacanth, galactan, carob gum, guar gum, karaya gum, carragheenin, pectin, agar, quince seed, starch, algae colloids, microbiological polymers, starch-based polymers, alginic acid-based polymers, acrylate polymers, inorganic water soluble materials, and combinations thereof.

Y. The container of paragraphs A-X, wherein the benefit phase is substantially free of a structurant.

Z. The container of paragraphs A-Y, wherein the viscosity of the cleansing phase is from about 1.0 to about 15 at 2 s−1 Pa·s and from about 0.1 to about 5 at 100 s−1 Pa·s.

AA. The container of paragraphs A-Z, wherein the aesthetic design is selected from the group consisting of bubbles, stripes, cross-hatching, zig-zag, floral, petal, herringbone, marbled, rectilinear, interrupted stripes, checked, mottled, veined, clustered, speckled, spotted, ribbons, helical, swirled, arrayed, variegated, waved, spiral, twisted, curved, streaks, laced, basket weaved, sinusoidal, and combinations thereof.

BB. The container of paragraphs A-AA, wherein the cleansing phase comprises a light transmission greater than 60%, preferably greater than 70%, and more preferably greater than 80% as measured by the Light Transmittance Method described hereafter.

CC. The container of paragraphs A-BB, further comprising from about 0.5 wt % to about 7 wt %, preferably from about 1.5 wt % to about 5 wt % of a rheology modifier selected from the group consisting of poly-acrylates, gellan gum, cellulose fibers, sodium polyacrylate starch, and mixtures thereof.

DD. The container of paragraphs A-CC, wherein the cleansing phase further comprises a silicone conditioning agent comprising an average particle size less than or equal to 30 nm.

EE. The container of paragraphs A-DD, wherein the density difference between the cleansing phase and the benefit phase is less than 0.30 g/cm3.

FF. The container of paragraphs A-EE, wherein the benefit phase further comprises a material selected from the group consisting of silicones comprising an average particle size greater than 30 nm, cationic deposition polymers, non-soluble anti-dandruff actives, and combinations thereof.

GG. The container of paragraphs A-FF, wherein a weight ratio of the cleansing phase to the benefit phase is from about 3:1 to about 97:3, preferably from about 4:1 to about 20:1, more preferably from about 4:1 to about 10:1, and even more preferably from about 4:1 to about 9:1.

HH. The container of paragraphs A-GG, wherein the multiphase shampoo composition comprises from about 5% to about 95%, preferably from about 10% to about 90%, and more preferably from about 20% to about 80%, by weight of the composition, cleansing phase.

II. A method of cleansing and conditioning hair comprising:
 a. providing the container of paragraphs A-HH wherein the container comprises a bottle configured to hold the multiphase shampoo composition and a pump configured to dispense the multiphase composition;
 b. activating the pump to dispense an amount of shampoo composition from the bottle;
 c. applying the shampoo composition to a user's hair;
 d. rinsing the shampoo composition from the hair.

JJ. The method of paragraph II, wherein the user's hair comprises a final rinse friction of less than 2000 gf, preferably less than 1750 gf, and more preferably less than 1700 gf, as determined using the Hair Wet Feel Friction Measurement described herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A container configured to hold a multiphase shampoo composition comprising:
   a. a cleansing phase comprising:
      i. a detersive surfactant;
      ii. a structurant, wherein the cleansing phase has a transmittance of at least 70%;
   b. a benefit phase comprising a gel network comprising:
      i. a fatty alcohol;
      ii. a secondary surfactant selected from the group consisting of anionic, amphoteric, zwitterionic, and combinations thereof;
   wherein the cleansing phase and the benefit phase are visually discrete phases, in physical contact, and form an aesthetic design suspended across at least a portion of the container;
   wherein the cleansing phase and the benefit phase are stable.

2. The container of claim 1, wherein the cleansing phase is substantially free of sulfate-based surfactants, and wherein the detersive surfactant is selected from the group consisting of isethionates, sarcosinates, sulfonates, sulfosuccinates, sulfoacetates, acyl glycinates, acyl alaninates, acyl glutamates, lactates, lactylates, glucose carboxylates, amphoacetates, taurates, phosphate esters, and mixtures thereof.

3. The container of claim 2, wherein the secondary surfactant is selected from the group consisting of amphoteric, zwitterionic, and combinations thereof.

4. The container of claim 3, wherein the secondary surfactant comprises a betaine.

5. The container of claim 1, wherein the cleansing phase comprises a yield stress of from about 0.01 to about 20 at a shear rate of 10-2 to 10-4 Pa (using Herschel Bulkley model).

6. The container of claim 1, wherein the structurant is selected from the group consisting of vinyl polymers, cellulose derivatives and modified cellulose polymers, polyvinylpyrrolidone, polyvinyl alcohol, guar gum, hydroxypropyl guar gum, xanthan gum, arabia gum, tragacanth, galactan, carob gum, guar gum, karaya gum, carragheenin, pectin, agar, quince seed, starch, algae colloids, microbiological polymers, starch-based polymers, alginic acid-based polymers, acrylate polymers, inorganic water soluble materials, and combinations thereof.

7. The container of claim 1, wherein the benefit phase is substantially free of a structurant.

8. The container of claim 1, wherein the cleansing phase comprises a yield stress of from about 0.01 to about 20 at a shear rate of 10-2 to 10-4 Pa, a viscosity of from about 1.0 to about 15 at 2 s-1 Pa·s, and a viscosity of from about 0.1 to about 4 at 100 s-1 Pa·s.

9. The container of claim 1, wherein the benefit phase further comprises a material selected from the group consisting of silicones comprising an average particle size greater than 30 nm, cationic deposition polymers, non-soluble anti-dandruff actives, and combinations thereof.

10. A container configured to hold a multiphase shampoo composition comprising:
    a. a cleansing phase comprising:
       i. a detersive surfactant;
       ii. a structurant;
    b. a benefit phase comprising a gel network comprising:
       i. a fatty alcohol;
       ii. a secondary surfactant selected from the group consisting of anionic, amphoteric, zwitterionic, cationic, and combinations thereof;
       iii. a cationic deposition polymer;
    wherein the cleansing phase and the benefit phase are visually discrete phases, in physical contact, and form an aesthetic design suspended across at least a portion of the container;
    wherein the cleansing phase and the benefit phase are stable; and
    wherein the container is a bottle comprising a transparent portion, and the bottle is substantially free of headspace and substantially free of visually discernable air bubbles prior of first use.

11. The container of claim 10, wherein the secondary surfactant is selected from the group consisting of anionic, amphoteric, zwitterionic, and combinations thereof.

12. The container of claim 10, wherein the benefit phase comprises form about 0.1% to about 1.0% of the cationic deposition polymer.

13. The container of claim 12, wherein the cationic deposition polymer has a weight average molecular weight of from about 300,000 g/mol to about 3,000,000 g/mol.

14. The container of claim 12, wherein the cationic deposition polymer is selected from the group consisting of cationic guars, cationic cellulose, cationic synthetic homopolymers, cationic synthetic copolymers, and combinations thereof.

15. The container of claim 12, wherein the cationic deposition polymer is selected from the group consisting of guar hydroxypropyltrimonium chloride, Polyquaternium 10, Polyquaternium 6, and combinations thereof.

16. A method of cleansing and conditioning hair comprising:
    a. providing the container of claim 10 wherein the container comprises a bottle configured to hold the multiphase shampoo composition and a pump configured to dispense the multiphase composition;
    b. activating the pump to dispense an amount of shampoo composition from the bottle;
    c. applying the shampoo composition to a user's hair; and
    d. rinsing the shampoo composition from the hair, wherein the user's hair comprises a final rinse friction of less than 2000 gf, according to the Hair Wet Feel Friction Measurement.

* * * * *